(12) United States Patent
Lomicka et al.

(10) Patent No.: US 9,433,506 B2
(45) Date of Patent: Sep. 6, 2016

(54) SPACER MOLDS FOR ORTHOPEDIC IMPLANTS

(71) Applicant: Zimmer, Inc., Warsaw, IN (US)

(72) Inventors: Matthew J. Lomicka, Fort Wayne, IN (US); Charlie Barfield, Southaven, MS (US); Michael Cordonnier, Carlsbad, CA (US); Dimitri Protopsaltis, Memphis, TN (US); Stephen Lingeman, Warsaw, IN (US); William Daniel, Southaven, MS (US); Terrance Strohkirch, Memphis, TN (US); Amber Lenz, Germantown, TN (US)

(73) Assignee: ZIMMER, INC., Warsaw, IN (US)

( * ) Notice: Subject to any disclaimer, the term of this patent is extended or adjusted under 35 U.S.C. 154(b) by 571 days.

(21) Appl. No.: 13/875,744

(22) Filed: May 2, 2013

(65) Prior Publication Data

US 2013/0295213 A1    Nov. 7, 2013

Related U.S. Application Data

(60) Provisional application No. 61/642,041, filed on May 3, 2012.

(51) Int. Cl.
*A61F 2/30* (2006.01)
*A61F 2/38* (2006.01)

(52) U.S. Cl.
CPC .............. *A61F 2/3094* (2013.01); *A61F 2/38* (2013.01); *A61F 2/389* (2013.01); *A61F 2/3859* (2013.01); *A61F 2/3872* (2013.01); *A61F 2002/30537* (2013.01); *A61F 2002/30556* (2013.01); *A61F 2310/00353* (2013.01)

(58) Field of Classification Search
CPC ........... A61F 2002/30957; A61F 2/38; A61F 2310/00353; A61F 2/3859; A61F 2/389; A61F 2002/3055; A61F 2250/0007; A61F 2/3094; A61F 2002/30693; B29C 33/10; B29C 33/308; B29C 39/26; B29C 45/66
USPC ............................ 425/577, 451.9, DIG. 221
See application file for complete search history.

(56) References Cited

U.S. PATENT DOCUMENTS

| | | | | |
|---|---|---|---|---|
| 4,552,287 A * | 11/1985 | Dziki | ............... | B05C 17/00533 425/458 |
| 5,882,691 A * | 3/1999 | Conboy | ............... | B05C 17/003 425/214 |
| 6,155,812 A * | 12/2000 | Smith | ................. | A61F 2/30942 425/318 |
| 7,127,769 B2 * | 10/2006 | Chang | ................... | E04F 21/165 425/458 |
| 8,414,286 B2 * | 4/2013 | Haney | ................. | A61F 2/30942 425/577 |

(Continued)

*Primary Examiner* — Jill Heitbrink
(74) *Attorney, Agent, or Firm* — Schwegman Lundberg & Woessner, P.A.

(57) ABSTRACT

A prosthetic mold for forming a prosthesis is disclosed. The prosthesis can include a bone mating surface, an articulating surface, and an intermedullary post. The prosthetic mold can include a first portion, a second portion engageable with the first portion, and an injection portion. The first portion can be configured to form the articulating surface. The second portion can be configured to form the bone mating surface and define an intermedullary post cavity. Engagement between the first and second portions can define a mold cavity. The injection port can be axially aligned, and in communication, with the intermedullary post cavity. The injection port can engage an injection assembly. In one embodiment, the prosthetic mold is configured to form a tibial prosthesis. In another embodiment, the prosthetic mold is configured to form a femoral prosthesis.

20 Claims, 38 Drawing Sheets

(56) References Cited

U.S. PATENT DOCUMENTS

| | | | |
|---|---|---|---|
| 8,419,401 B2* | 4/2013 | McMahon | B05C 17/00503 425/458 |
| 8,920,152 B2* | 12/2014 | Hawkins | 425/470 |
| 9,022,767 B2* | 5/2015 | Oono | B29C 45/1751 425/150 |
| 9,056,011 B2* | 6/2015 | Stolarski | A61F 2/30942 |

\* cited by examiner

SPACER MOLDS FOR ORTHOPEDIC IMPLANTS

CLAIM OF PRIORITY

This patent document claims the benefit of priority of U.S. Provisional Patent Application Ser. No. 61/642,041, entitled "SPACER MOLDS FOR ORTHOPEDIC IMPLANTS," filed on May 3, 2012, which is hereby incorporated by reference in its entirety.

TECHNICAL FIELD

The present disclosure relates to molds for forming orthopedic implants. More particularly, but not by way of limitation, the present disclosure relates to molds for forming temporary spacer tibial or femoral implants.

BACKGROUND

It is possible for tissue surrounding orthopedic implants, such as knee or hip implants, to become infected. If necessary, the implant is removed, and it may take several weeks or more to adequately treat the infection, during which time the implant site is kept immobile. Immobility can result in soft tissue contraction and loss of range of motion of the joint previously occupied by the implant.

To prevent one or both of tissue contraction and loss of range of motion, an articulating temporary implant or spacer, typically made of an antibiotic-filled cement, can be used to fill the space previously occupied by the implant while the infection is being treated. Once the temporary implant is positioned, the antibiotic leaches out of the spacer to aid in treatment of tissues near the spacer and prevent further spreading of the infection. Once the infection is cleared, the spacer can be replaced with a new permanent implant.

SUMMARY

The present disclosure provides molds for forming a temporary spacer implant. In one embodiment, a mold for forming a temporary femoral implant is disclosed. In another embodiment, a mold for forming a temporary tibial implant is disclosed.

More particularly, according to a first embodiment, a spacer mold for forming a temporary prosthesis having an interior bone mating surface, an exterior articulating surface, and an intermedullary post is provided. The mold can comprise a first portion configured to form the exterior articulating surface, a second portion configured to form the interior bone mating surface and the intermedullary post, a plurality of removable locking members securing the first portion to the second portion, and an injection port axially aligned with the formed intermedullary post. The locking members can include a C-shaped channel configured to cooperate with a first protrusion on the first portion and a second protrusion on the second portion to secure the first portion to the second portion during injection of cement through the injection port.

According to a second embodiment, a spacer mold for forming a temporary tibial prosthesis having an interior bone mating surface, an exterior articulating surface, lateral and medial dished articular components, and an intermedullary post is provided. The mold can comprise a bottom portion configured to form the exterior articulating surface, a top portion secured to the bottom portion by a plurality of removable locking members, and a plunger configured to form the interior bone mating surface and the intermedullary post. A position of the plunger, relative to the bottom portion, can be configured for continuous adjustability between a maximum distance and a minimum distance.

According to a third embodiment, a spacer mold for forming a temporary femoral prosthesis having an interior bone mating surface, an exterior articulating surface, an anterior flange, lateral and medial posterior condyles, a rounded articulated portion, and an intermedullary post is provided. The mold can comprise a top portion configured to form the interior bone mating surface and the intermedullary post of the prosthesis, a bottom portion configured to form the exterior articulating surface of the prosthesis, a plurality of removable locking members securing the top portion to the bottom portion; and an injection port axially aligned with the intermedullary post of the formed prosthesis.

To better illustrate the prosthetic spacer molds disclosed herein, a non-limiting list of embodiments is provided here:

In Embodiment 1, a prosthetic mold for forming a prosthesis having a bone mating surface, an articulating surface and an intermedullary post, can comprise a first portion configured to form the articulating surface, and a second portion engageable with the first portion to define a mold cavity therebetween. The second portion can be configured to form the bone mating surface and define an intermedullary post cavity. An injection port can be axially aligned, and in communication, with the intermedullary post cavity, and can be configured to engage an injection assembly.

In Embodiment 2, the prosthetic mold of Embodiment 1 can optionally be configured to comprise a post-injection assembly configured to be removably coupled to the injection port. The post-injection assembly can include a handle and a stem having at least one channel in fluid communication with the mold cavity.

In Embodiment 3, the prosthetic mold of Embodiments 1 and 2 can optionally be configured to comprise at least one locking member configured to contemporaneously engage at least one first protrusion, disposed on the first portion, and at least one second protrusion, disposed on the second portion, to secure the first and second portions to each other.

In Embodiment 4, the prosthetic mold of Embodiment 3, can optionally be configured such that the first and second portions further include a first and a second disengagement member, respectively, the at least one locking member configured to separately engage the first and the second disengagement member.

In Embodiment 5, the prosthetic mold of Embodiments 3 and 4 can optionally be configured such that the at least one locking member is configured to provide a planar surface for positioning the mold in an upright position.

In Embodiment 6, the prosthetic mold of any one or any combination of Embodiments 1 through 5 can optionally be configured such that the second portion comprises a plunger configured to form the bone mating surface and define the intermedullary post cavity, and a cover configured to fit over the plunger and engage the first portion.

In Embodiment 7, the prosthetic mold of Embodiment 6 can be optionally configured such that a position of the plunger, relative to the first portion, is adjustable among a plurality of positions between a predetermined maximum distance and a predetermined minimum distance.

In Embodiment 8, the prosthetic mold of Embodiment 7 can optionally be configured to comprise an adjustment mechanism engaged with the plunger and configured to continuously adjust the plunger among the plurality of positions.

In Embodiment 9, the prosthetic mold of Embodiment 8 can be optionally configured such that the adjustment mechanism comprises a dial having a threaded surface configured to cooperate with a threaded surface of the plunger.

In Embodiment 10, the prosthetic mold of any one or any combination of Embodiments 7 through 9 can be optionally configured such that the plunger further comprises a plurality of indicia corresponding to a plurality of dimensions of the mold cavity, as measured when the plunger is in one of the plurality of adjustable positions.

In Embodiment 11, the prosthetic mold of Embodiment 10 can be optionally configured such that the plurality of dimensions correspond to a plurality of distances between the bone mating surface and a region of the first portion corresponding to a low point in the articular surface of the prosthesis.

In Embodiment 12, a prosthetic mold for forming a prosthesis having a bone mating surface and an articulating surface, can comprise a cavity member configured to form the articulating surface, and a plunger having a surface configured to form the bone mating surface. The plunger can be configured to fit within the cavity member and define a mold cavity.

In Embodiment 13, the prosthetic mold of Embodiment 12 can be optionally configured such that a position of the plunger, relative to the cavity member, is adjustable among a plurality of positions between a predetermined maximum distance and a predetermined minimum distance.

In Embodiment 14, the prosthetic mold of Embodiments 12 and 13 can be optionally configured to further comprise an adjustment mechanism engaged with the plunger and configured to continuously adjust the plunger among the plurality of positions.

In Embodiment 15, the prosthetic mold of Embodiment 14 can be optionally configured such that the adjustment mechanism comprises a dial having a threaded surface configured to cooperate with a threaded surface of the plunger.

In Embodiment 16, the prosthetic mold of any one or any combination of Embodiments 13 through 15 can optionally be configured such that the plunger further comprises a plurality of indicia corresponding to a plurality of dimensions of the mold cavity, as measured when the plunger is in one of the plurality of positions.

In Embodiment 17, the prosthetic mold of claim 16 can optionally be configured such that the plurality of dimensions correspond to a plurality of distances between the bone mating surface and a region of the cavity member corresponding to a low point in the articular surface of the prosthesis.

In Embodiment 18, the prosthetic mold of any one or any combination of Embodiments 13 through 17 can be optionally configured to further comprise a stop mechanism configured to engage the plunger to fix the position of the plunger within the mold cavity.

In Embodiment 19, the prosthetic mold of any one or any combination of Embodiments 12 through 18 can be optionally configured to further comprise a compression mechanism engaged with the plunger, the cavity member, or both, and configured to press the plunger into the cavity member.

In Embodiment 20, the prosthetic mold of Embodiment 19 can be optionally configured such that the compression mechanism comprises a cover, an adjustment dial, or a compression rod.

These and other examples and features of the present prosthetic spacer molds and related kits and methods are set forth in part in the following Detailed Description. This Overview is intended to provide non-limiting examples of the present subject matter—it is not intended to provide an exclusive or exhaustive explanation. The Detailed Description below is included to provide further information about the present prosthetic spacer molds and related kits and methods.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings.

In the drawings, like numerals can be used to describe similar elements throughout the several views. Like numerals having different letter suffixes can be used to represent different views or features of similar elements. The drawings illustrate generally, by way of example, but not by way of limitation, various embodiments discussed in the present patent document.

DETAILED DESCRIPTION

Figure 1A:
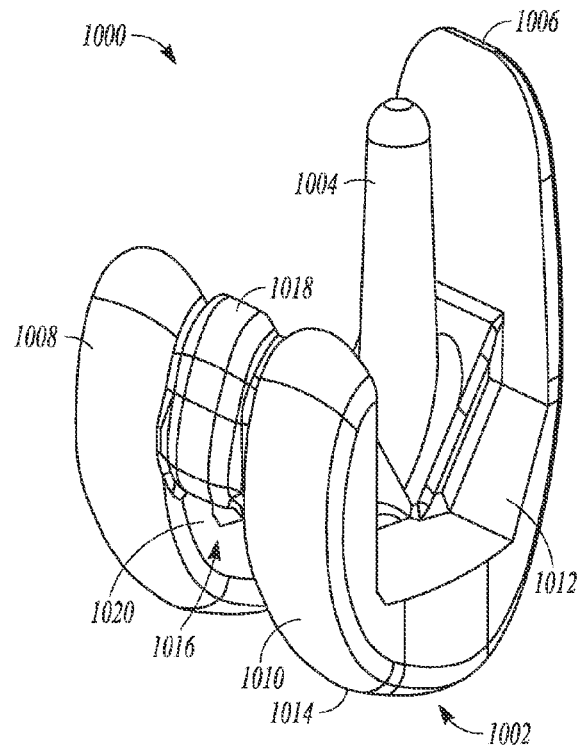
FIG. 1A is a perspective view of a temporary femoral spacer produced from a femoral spacer mold in accordance with the present disclosure.

The present disclosure provides molds for forming a component of a temporary knee prosthesis.

As used herein, "proximal" refers to a direction generally toward the torso of a patient, and "distal" refers to the opposite direction of proximal, i.e., away from the torso of a patient. "Anterior" refers to a direction generally toward the front of a patient or knee, and "posterior" refers to the opposite direction of anterior, i.e., toward the back of the patient or knee. In the context of a prosthesis, such directions correspond to the orientation of the prosthesis after implantation, such that a proximal portion of the prosthesis is that portion which will ordinarily be closest to the torso of the patient, the anterior portion closest to the front of the patient's knee, etc.

Similarly, knee prostheses in accordance with the present disclosure may be referred to in the context of a prosthesis coordinate system including three mutually perpendicular reference planes, referred to herein as the transverse, coronal and sagittal planes of the knee prosthesis. Upon implantation and with a patient in a standing position, a transverse plane of the knee prosthesis is generally parallel to an anatomic transverse plane, i.e., the transverse plane is inclusive of imaginary vectors extending along medial/lateral and anterior/posterior directions. Coronal and sagittal planes of the knee prosthesis are also generally parallel to the coronal and sagittal anatomic planes in a similar fashion. Thus, a coronal plane of the prosthesis is inclusive of vectors extending along proximal/distal and medial/lateral directions, and a sagittal plane is inclusive of vectors extending along anterior/posterior and proximal/distal directions. As with anatomic planes, the sagittal, coronal and transverse planes of a knee prosthesis are mutually perpendicular to one another. For purposes of the present disclosure, reference to sagittal, coronal and transverse planes is with respect to a knee prosthesis unless otherwise specified.

The embodiments shown and described herein illustrate a right knee temporary prosthesis. Right and left knee temporary prosthesis configurations are mirror images of one another about a sagittal plane. Thus, it will be appreciated that the aspects of the temporary prosthesis described herein are equally applicable to a left or right knee configuration.

As used herein, the term "cement" generally refers to any curing and hardening material suitable for implanted spacers. The cement may be loaded with an antibiotic such as Gentamicin, Vancomycin, Tobramycin and/or Clindamycin in order to clear infection from tissue surrounding an implanted spacer formed by a spacer mold in accordance with the present disclosure. Exemplary cement is described in the "Zimmer® Bone Cement and Accessories" brochure, copyright 2006, published by Zimmer, Inc., the entire disclosure of which is hereby expressly incorporated herein by reference. This includes materials such as Palacos® R+G High Viscosity Bone Cement and any other similar material.

In one form, a spacer mold can be releasably connectable to a nozzle of a cement gun that uses pressurized cartridges of cement. The term "direct injection molds" can include spacer molds connectable to a cement gun in which cement is injected into a cavity of the spacer mold from a cement cartridge attached to the cement gun. The cement gun can eject cement or curable material from a cartridge such as high-strength, high-viscosity poly-methyl-methacrylate (PMMA).

In another form, cement can be prepared external to a spacer mold and applied to a cavity of the spacer mold prior to the mold being assembled. The term "compression molds" can include spacer molds that do not receive cement from a cement gun.

In still another form, the disclosed spacer molds can be designed to be disposable after a single use. Disposable spacer mold technologies prevent medical practitioners from being burdened with the cleaning and sterilization procedures required to reuse surgical instruments, which can be expensive and time consuming.

Figure 1B:
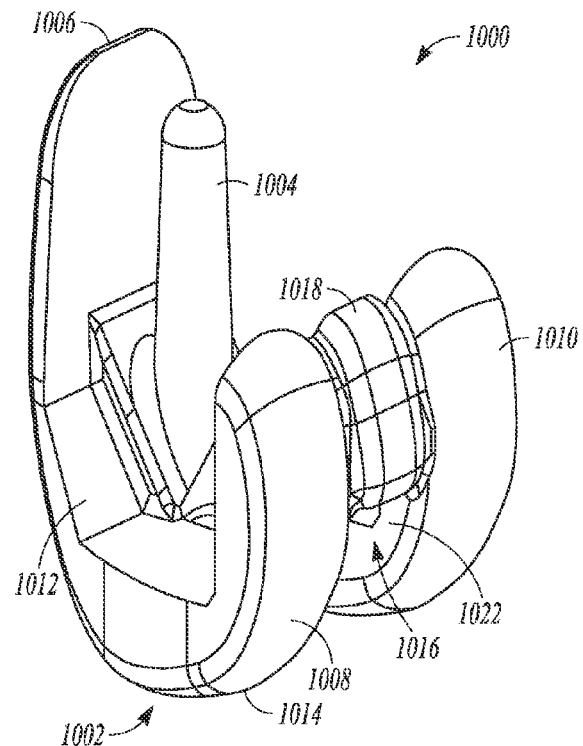
FIG. 1B is another perspective view of the femoral spacer of FIG. 1A.

Referring first to FIGS. 1A-1B, an exemplary femoral spacer 1000, produced from a femoral spacer mold 10 in accordance with the present disclosure, is illustrated. The femoral spacer 1000 can include a rounded, articulated portion 1002 to interface with a tibial implant, such as a tibial spacer 1100 illustrated in FIG. 29. The femoral spacer 1000 can also include an intermedullary post 1004 extending from the articulated portion 1002. The intermedullary post 1004 can be inserted into a medullary canal on a patient's femur, allowing the femoral spacer 1000 to be anchored to the bone. The femoral spacer 1000 can further include an anterior flange 1006, a medial posterior condyle 1008, and a lateral posterior condyle 1010. An interior bone mating surface 1012 can be provided on a first side of the femoral spacer 1000, and an exterior articulating surface 1014 can be provided on a second side of the femoral spacer 1000.

The femoral spacer 1000 can include a femoral cam 1018 spanning an intercondylar notch 1016 formed between a medial posterior condyle 1008 and a lateral posterior condyle 1010. Condylar walls 1020 and 1022 can be engagable with a spine 1106 of the tibial spacer 1100 (FIG. 29) to provide medial and lateral stability to the femoral spacer 1000 from full extension to at least mid-flexion. As illustrated, the condylar walls 1020 and 1022 can be substantially parallel across the intercondylar notch 1016. The femoral cam 1018 can be sized, shaped, and positioned to articulate with the spine 1106 of the tibial spacer 1100 (FIG. 29) along the articulating surface 1108. Other exemplary femoral implants are disclosed in U.S. Patent Publication No. 2010/0102484, the disclosure of which is hereby incorporated by reference in its entirety.

Figure 2:
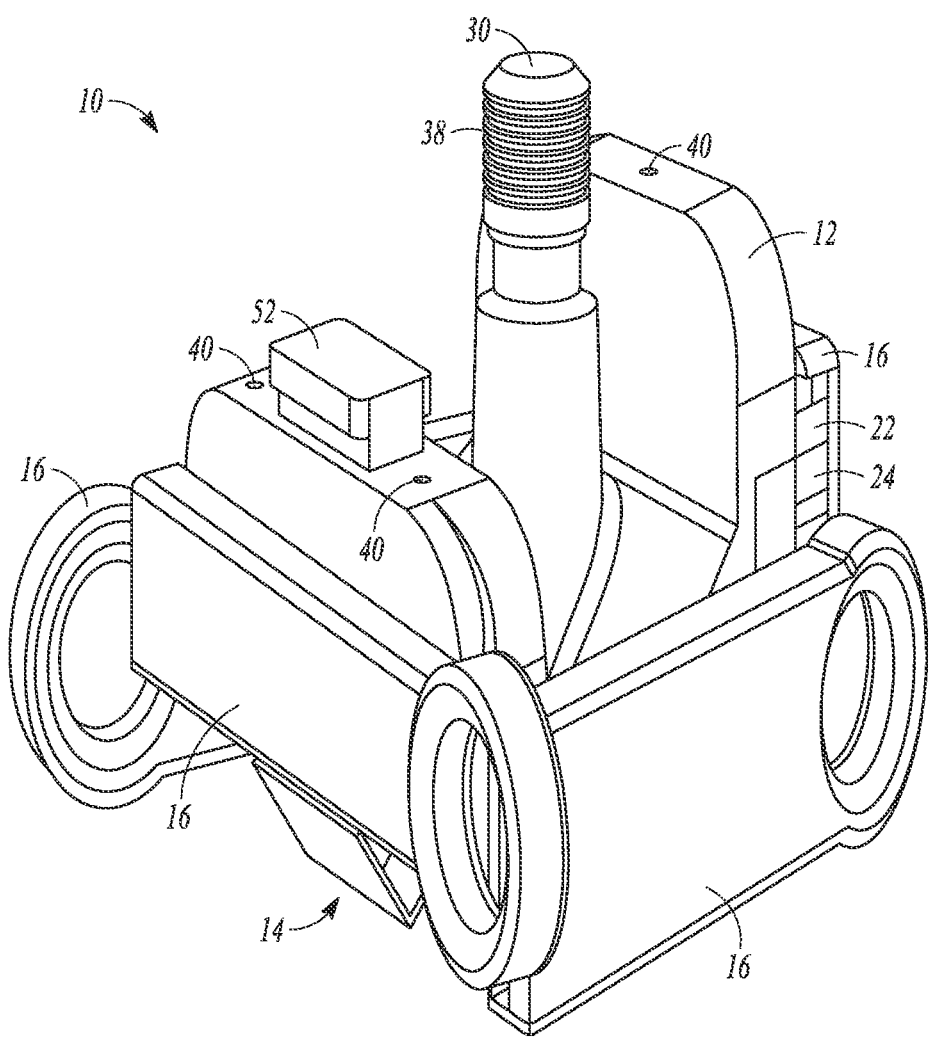
FIG. 2 is a perspective view of a femoral spacer mold in accordance with the present disclosure.
Figure 3:
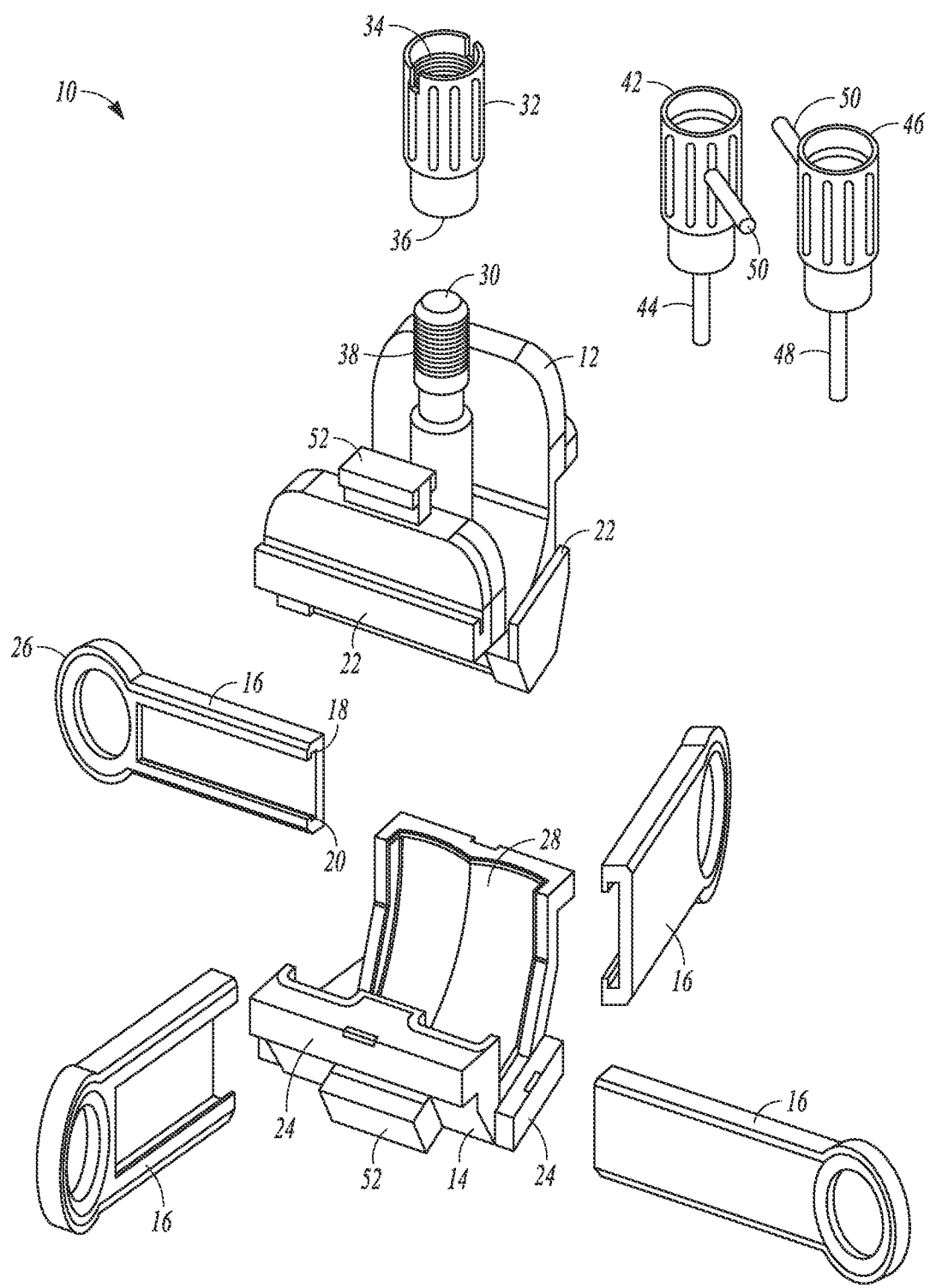
FIG. 3 is an exploded perspective view of the femoral spacer mold of FIG. 2.
Figure 4:
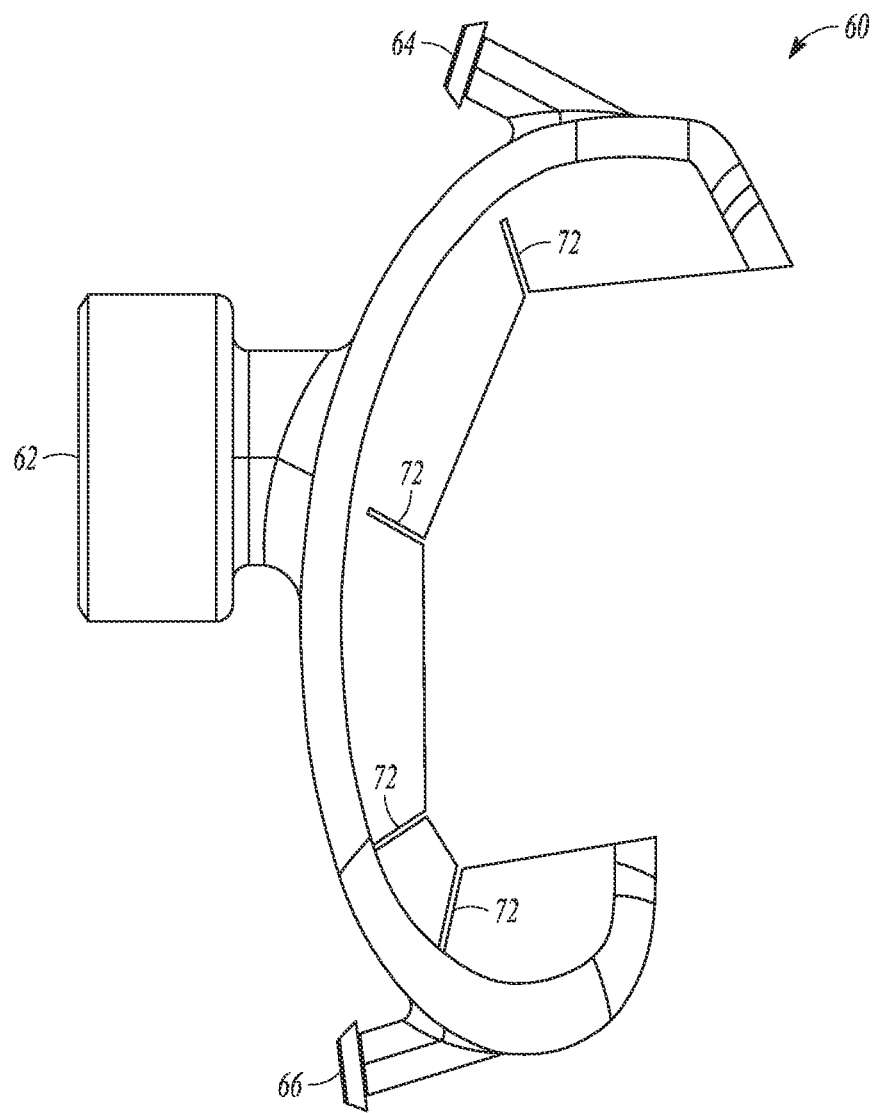
FIG. 4 is a side view of an on-knee femoral spacer mold including water cooling in accordance with the present disclosure.
Figure 5:
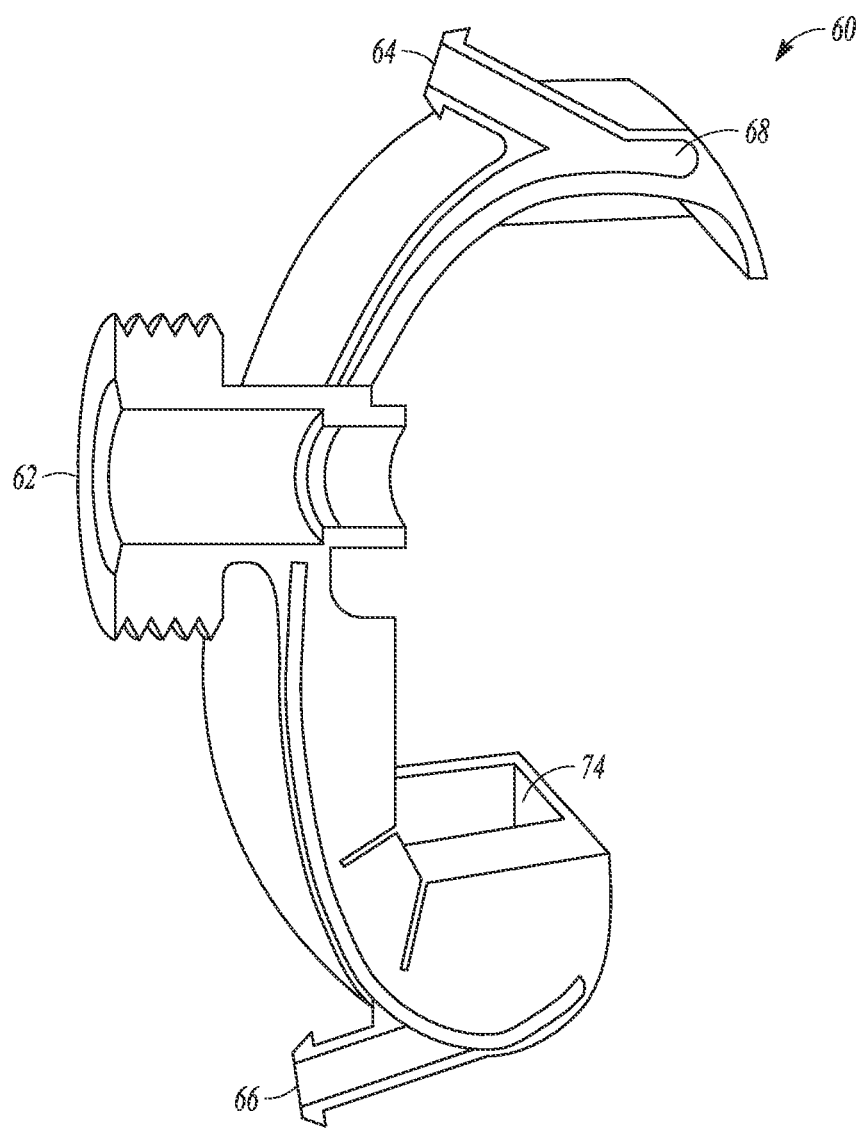
FIG. 5 is a sectional perspective view of the on-knee femoral spacer mold of FIG. 4.

Referring next to FIGS. 2-3, an exemplary femoral spacer mold 10 in accordance with the present disclosure is illustrated. The femoral spacer mold 10 can include a top portion 12 and a bottom portion 14, held together using a plurality of locking members 16. As illustrated, the locking members 16 can include a plurality of C-channel locking members. Other suitable numbers and types of locking members 16 can also be used. The mold 10 can be presented to a surgeon fully assembled and ready for cement injection.

As illustrated in FIGS. 2 and 3, the locking members 16 can each include a top edge 18 and a bottom edge 20. The top edge 18 can fit around a protrusion 22 on the top portion 12. The bottom edge 20 can fit around a protrusion 24 on the bottom portion 14. When the top portion 12 and the bottom portion 14 are assembled, as in FIG. 1, the top edge 18 and the bottom edge 20 of the locking members 16 can cooperate to secure the top portion 12 and the bottom portion 14. The locking members 16 can also include a grip 26 to allow easy movement of the locking members 16. As illustrated, the grip 26 can be a ring formed on one end of the locking members 16, but other suitable grips can also be used. As illustrated, the locking members 16 and the bottom portion 14 cooperate to form a plurality of points along a plane. The mold 10 can rest on this plane in an upright orientation during cement injection and curing.

A cavity 28 can be defined in the space between the top portion 12 and the bottom portion 14 of the mold 10, when assembled. An injection port 30 provides access to the cavity 28 to receive cement injected from a cement gun or other injector of pressurized, curable material. Cement can be provided from a cartridge of a cement gun at a pressure sufficient to spread the cement to substantially fill the interior of the mold 10. Specifically, the cement can fill the entirety of cavity 28 from the injection port 30, thereby forming the femoral spacer 1000 (FIG. 1).

The injection port 30 and the remainder of the mold 10 can have sufficient rigidity to receive the cement under high pressure without compromising the connection between the injection port 30 and the cement source or breaking, splitting, or cracking the mold 10 when the pressurized cement is received. For these purposes, in one form, high density polyethylene can be used to form the mold 10.

In one form, the cement is received through an adaptor plug 32 into the injection port 30. The adaptor plug 32 can include first internal threads 34, configured to mate with external threads on a cement gun or other cement source, and second internal threads 36, configured to mate with external threads 38 on the injection port 30. The injection port 30 can be axially aligned with the intermedullary post 1004.

As shown in FIG. 2, the mold 10 can include vent holes 40 communicating with the cavity 28 at positions corresponding to the proximal ends of the anterior flange 1006 and the posterior condyles 1008, 1010 of the femoral spacer 1000 (FIG. 1). The vent holes 40 can be configured to allow air to exit the cavity 28 and allow cement to fully fill the cavity 28. During filling, once cement begins to exit the vent holes 40, the mold 10 is full. The cement gun and adaptor plug 32 can then be removed.

Referring again to FIG. 3, a cleaning plug 42 can be attached to the injection port 30. The cleaning plug 42 can include a stem 44 that clears excess cement from the injection area before the cement cures and becomes stuck to the femoral spacer 1000. The cleaning plug 42 can include one or more channels (shown in FIGS. 42 and 43) allowing cement to flow up into a hollow space in the cleaning plug 42. In an exemplary embodiment, the cleaning plug 42 can include three channels around the stem 44.

Once the cement has fully cured, the locking members 16 can be removed from the protrusions 22, 24 by sliding them off. The cleaning plug 42 can be removed from the injection port 30. The ejection plug 46, having a stem 48 longer than the stem 44 of the cleaning plug 42, can then attached to the injection port 30. As the ejection plug 46 is inserted onto the injection port 30, the stem 48 can engage and place a downward force on the cured femoral spacer 1000 in the cavity 28. Because the locking members 16 have been removed, the top portion 12 and the bottom portion 14 can be separated by the downward force of the stem 48. The plugs 42, 46 can include a handle 50 to assist in inserting the plugs 42, 46 onto the injection port 30.

If the downward force of the stem 48, from the ejection plug 46, fails to separate the top portion 12 and the bottom portion 14, the locking members 16 can be attached to disassembly tabs 52 on the top portion 12 and the bottom portion 14. Force can be applied to a disassembly tab 52 on the top portion 12, through a first locking member 16, and to a disassembly tab 52 on the bottom portion 14, through a second locking member 16 to pull the mold portions 12, 14 apart. Once the mold portions 12, 14 are separate, the femoral spacer 1000 can be removed from the mold 10.

Figure 6:
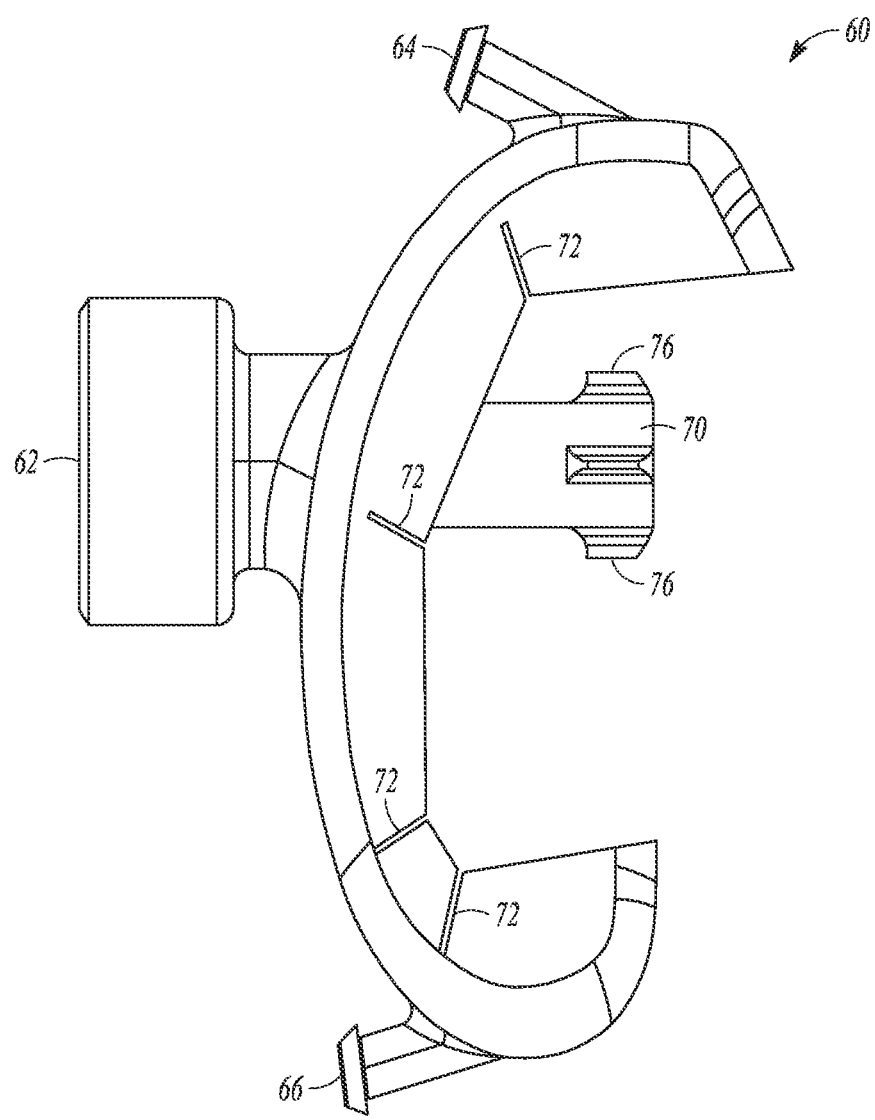
FIG. 6 is side view of the on-knee femoral spacer mold of FIG. 5 including a stem component.

Referring next to FIGS. 4-7, an on-knee femoral mold 60 including water cooling is illustrated. The mold 60 can include an injection port 62, a water inlet 64, a water outlet 66, and a water chamber 68. As shown in FIG. 6, the mold 60 can also include a stem component 70. The stem component 70 can be made of plastic. Molding can take place directly on a femur of the patient. A plurality of slits 72 can be included on the mold to allow the mold to flexibly fit around the femur. Once the mold is positioned on the femur, a cement gun can be attached to a rigid injector port, and cement can be injected through the mold, filling the cavity 74 formed between the bone and the mold 60 to form a femoral spacer 1000. Water or another suitable coolant fluid can be fed into the water inlet 64, through the mold in the water chamber 68, and out of the water outlet 66, while the cement femoral spacer is curing. Once the cement is cured, the mold can be removed.

Figure 7:
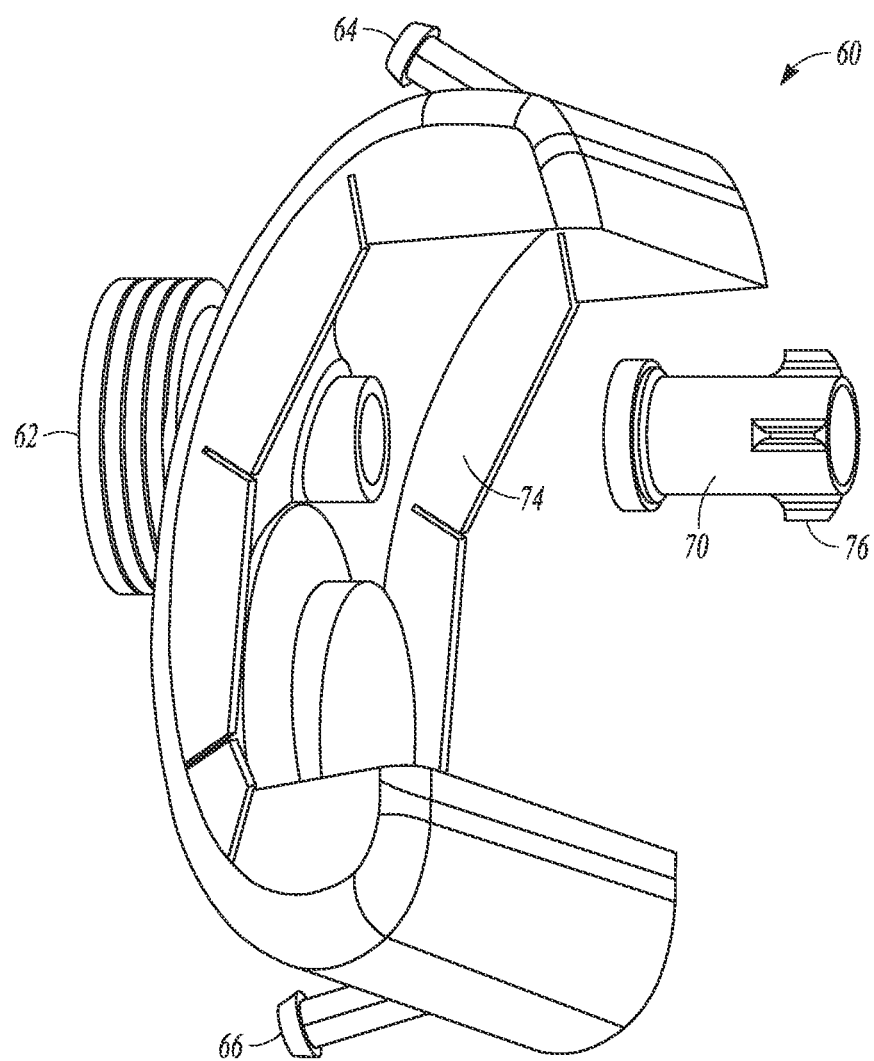
FIG. 7 is a partially exploded perspective view of the on-knee femoral spacer mold of FIG. 6.

In one form, the mold 60 and the stem component 70 can be positioned so that the stem component 70 is inserted into a medullary canal on a patient's femur. Cement passes through the injection port 62 and the stem component 70, then between the outside of stem component 70 and the patient's bone to fill the cavity 74, thereby forming the femoral spacer 1000. As shown in FIG. 7, the stem component 70 can detach from the remainder of the mold 60 after the cement has cured and remains in the femoral spacer 1000 as part of the intermedullary post 1004. A plurality of fins 76 on the stem can provide increased stability for the stem component 70 in the formed intermedullary post 1004.

Figure 8:
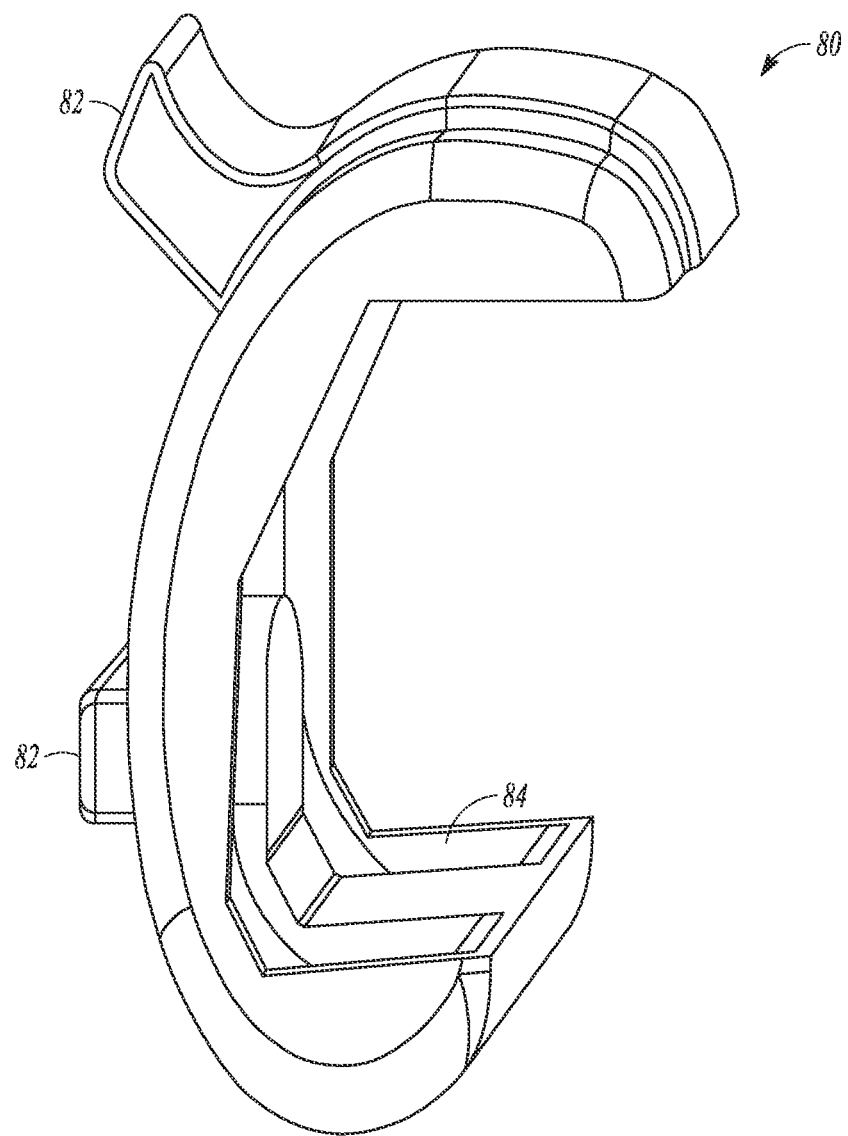
FIG. 8 is a perspective view of a flexible on-knee femoral spacer mold in accordance with the present disclosure.
Figure 9:
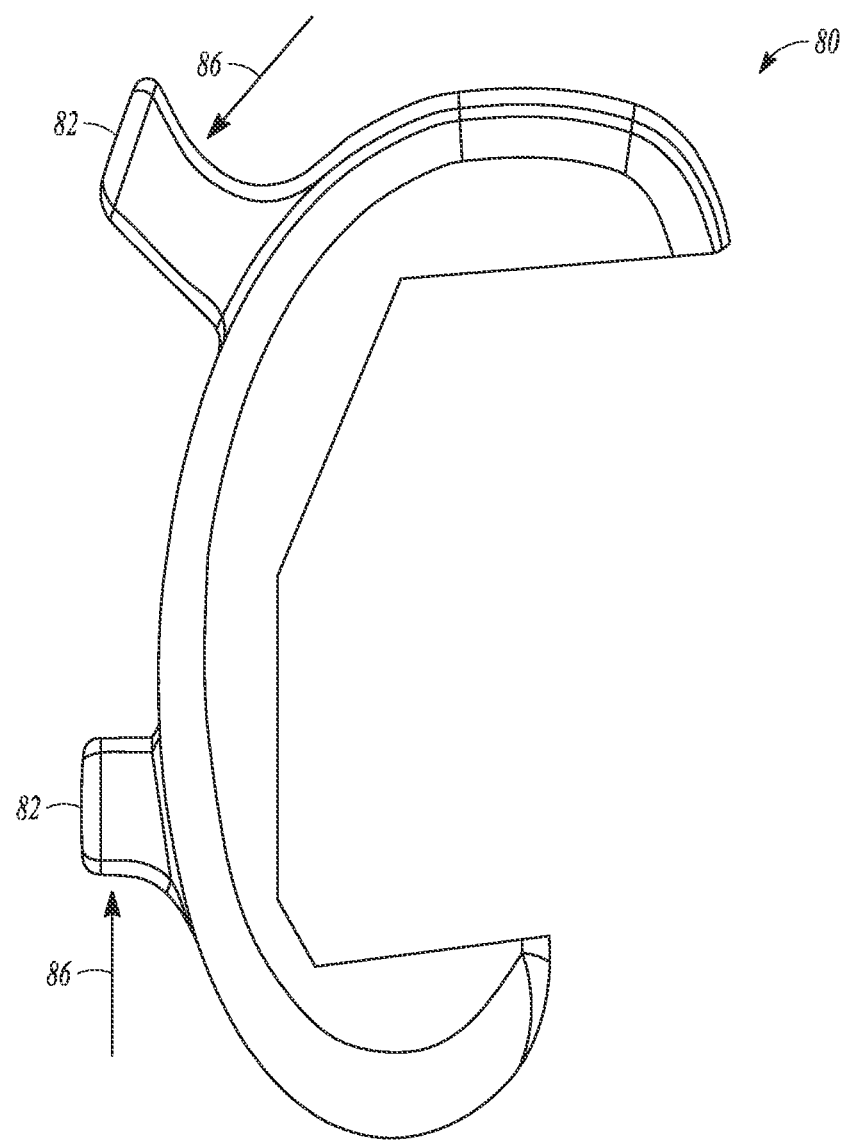
FIG. 9 is a side view of the flexible on-knee femoral spacer mold of FIG. 8.

Referring next to FIGS. 8-9, another on-knee femoral mold 80 is illustrated. The mold 80 can includes tabs 82 for removal of the mold. Cement can be placed into a cavity 84, filling the cavity, and then the mold 80 can be placed directly on the bone for curing. After the cement has cured, force can be applied to the tabs 82 in the directions indicated by arrows 86, flexing open the mold 80 and allowing it to be removed from the bone.

Figure 10:
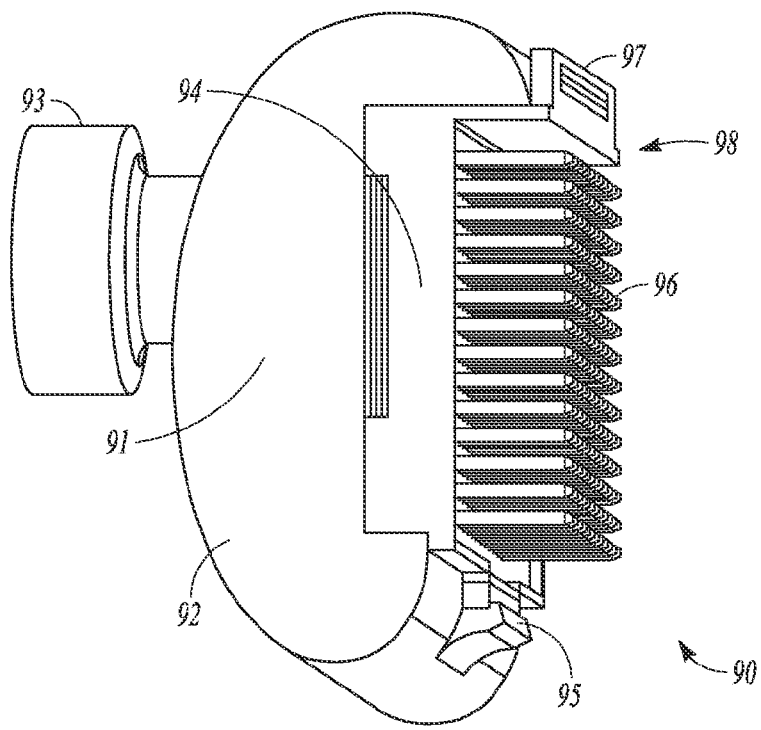
FIG. 10 is a perspective view of a femoral contour replication device and femoral spacer mold in accordance with the present disclosure
Figure 11:
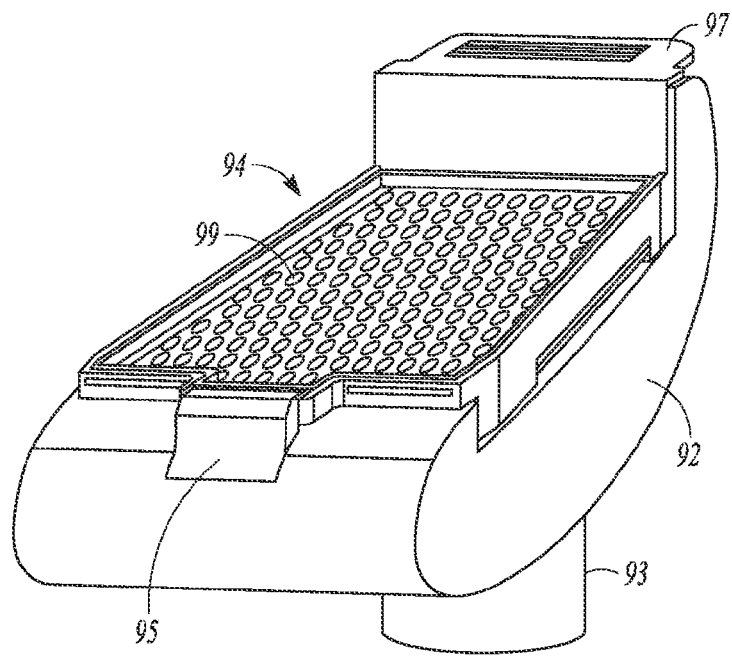
FIG. 11 is another perspective view of the femoral contour replication device and femoral spacer mold of FIG. 10.
Figure 12:
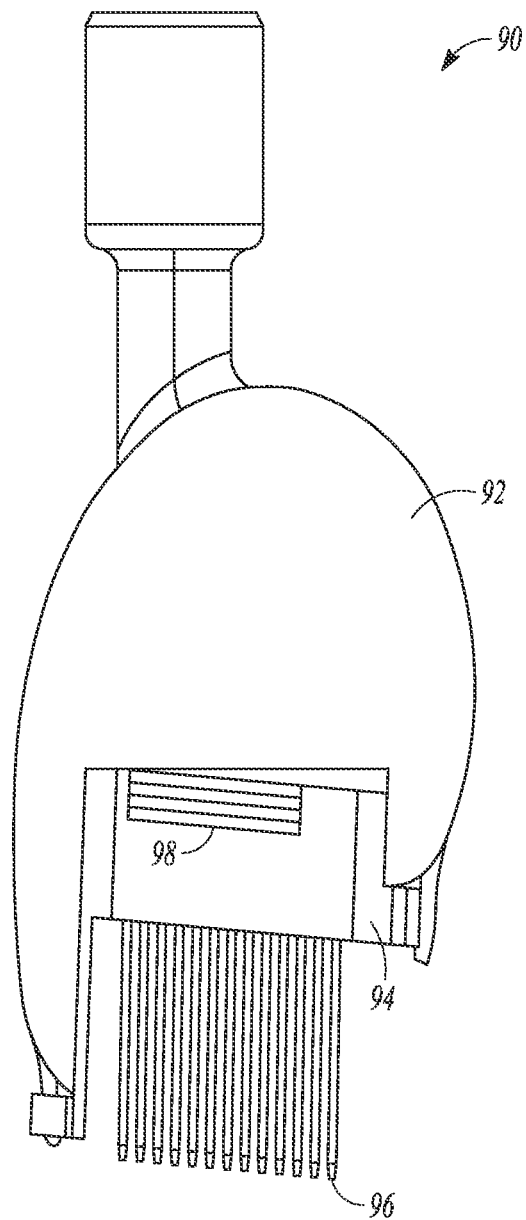
FIG. 12 is a side view of the femoral contour replication device and femoral spacer mold of FIG. 10.
Figure 13:
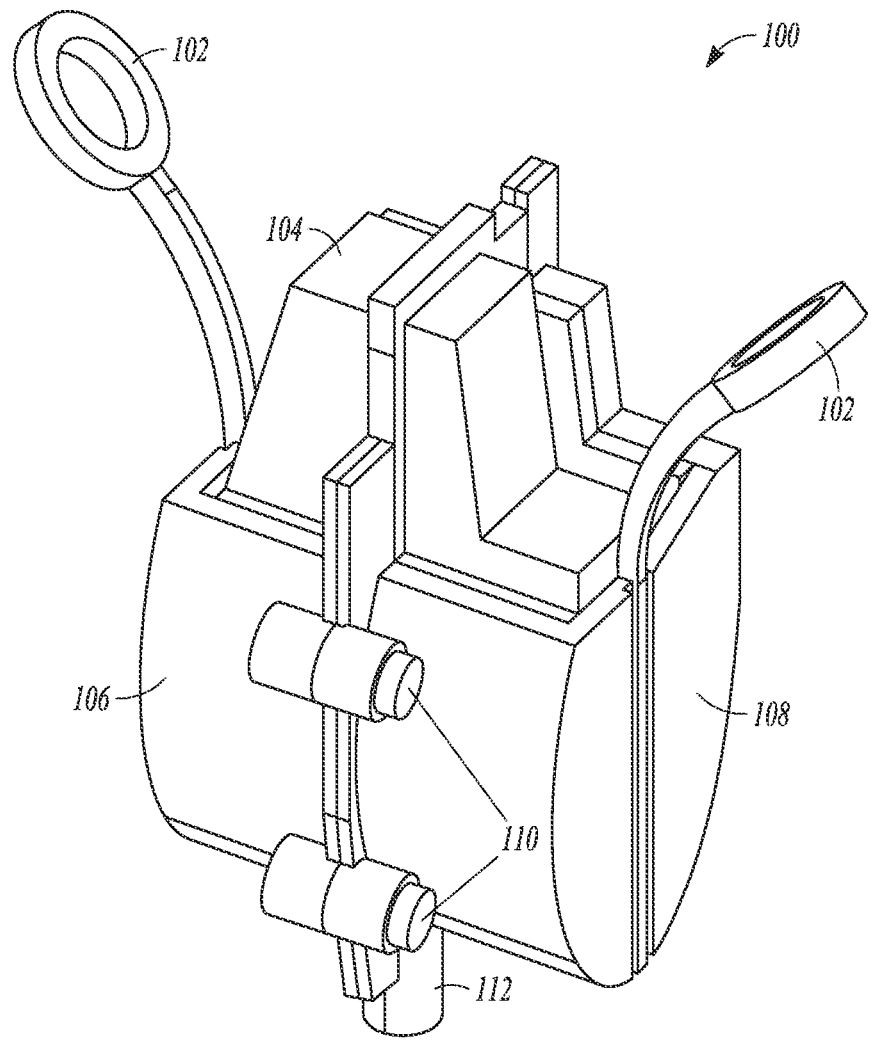
FIG. 13 is a perspective view of a femoral injection mold including pull-tabs in accordance with the present disclosure.
Figure 14:
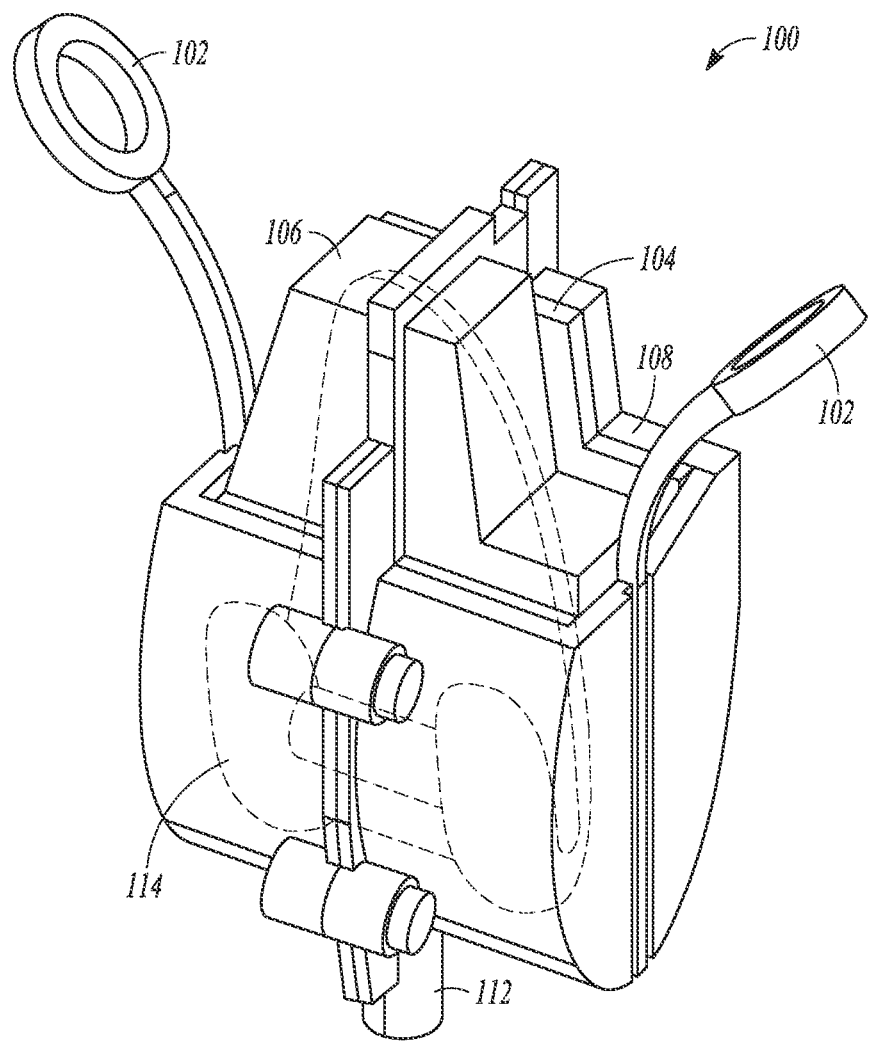
FIG. 14 is a transparent perspective view of the femoral injection mold of FIG. 13.
Figure 15:
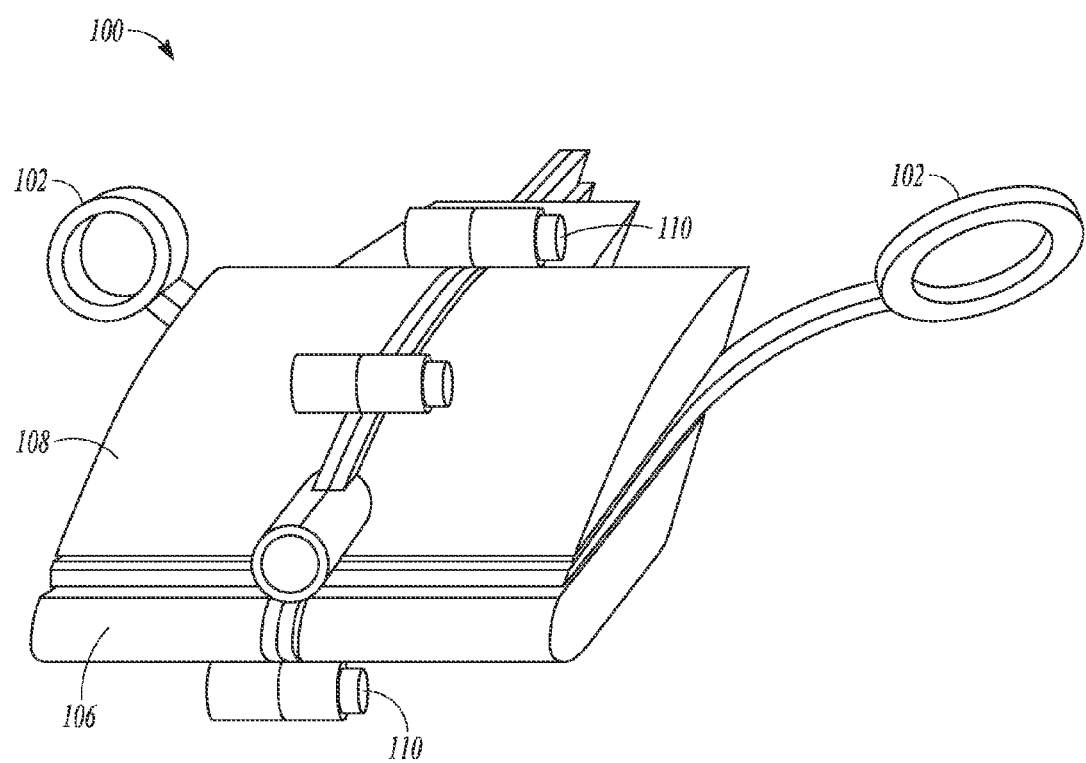
FIG. 15 is a bottom perspective view of the femoral injection mold including pull-tabs of FIG. 13.
Figure 16:
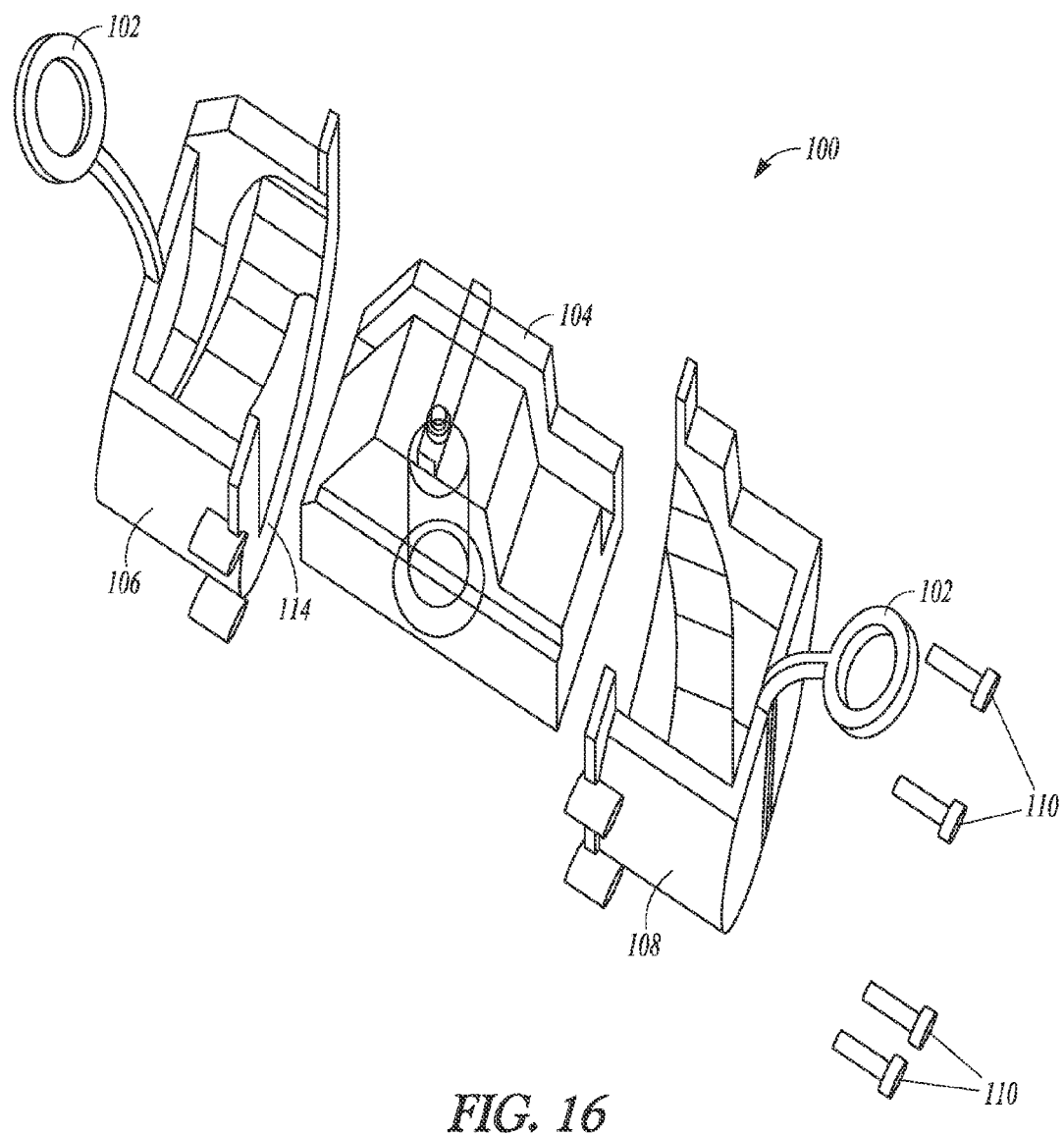
FIG. 16 is an exploded top perspective view of the femoral injection mold including pull-tabs of FIG. 13.

Referring next to FIGS. 10-12, a femoral contour replication device 90 is illustrated. Femoral contour replication device 90 can be used with a femoral mold 92. The femoral mold 92 can be one of on-knee femoral molds 60, 80. As illustrated, the femoral mold 92 can be similar to mold 60, but may not include water cooling or slits. The femoral mold 92 can include an injection port 93 for injecting cement into the mold, although, in other embodiments, a compression mold can be used. In the illustrated embodiment, the femoral mold 92 can also include a closed shoulder 91 to contain cement in an interior space of the femoral mold 92. The femoral contour replication device 90 can include a pin device 94 that includes a plurality of pins 96 arranged in a plurality of pin holes 99 (see FIG. 11) covered with a flexible membrane. FIG. 11 illustrates the femoral contour replication device 90 and the femoral mold 92 with pins 96 removed to show an exemplary pin arrangement. Additional exemplary pin arrangements are shown in FIGS. 10 and 12, but other suitable arrangements may also be used. The pins 96 of the femoral contour replication device 90 can be pressed up against the femur of the patient, and the femoral contour replication device 90 can take on the shape and contour of the femur. A locking device 98 can lock the pins 96 into position, holding the shape and contour of the femur. In one exemplary embodiment, the locking device 98 can be a toggle switch shifting an interior plate of the pin device 94, securing the pins 96 in position, but other suitable locking devices can also be used. The femoral contour replication device 90 can be inserted into the femoral mold 92, forming a closed mold. In one embodiment, the femoral contour replication device 90 can be attached to the femoral mold 92 using attachments 95 and 97, although other suitable securing arrangements can also be used. Cement can then be inserted into the mold, as with other femoral molds herein described. Because the pins 96 are locked into the shape and contour of the femur by the locking device 98, and this surface forms one side of the molded femoral spacer 1000, the femoral spacer 1000 can include an interior bone mating surface 1012 that matches the patient's bone surface.

FIGS. 13-16 illustrate a femoral injection mold 100 including pull tabs 102. The mold 100 can comprise an inner form block 104, a first outer component 106, and a second outer component 108. The inner form block 104 can form a femoral spacer intermedullary post 1004 and interior bone mating surfaces 1012. The first outer component 106 and the second outer component 108 can form exterior articulating surfaces 1014 of the femoral spacer 1000. The inner form block 104, the first outer component 106, and the second outer component 108 can define a cavity 114, when assembled. The first outer component 106 and the second outer component 108 can be held together by a plurality of screws 110. In one form, the inner form block 104 can fit inside the first outer component 106 and the second outer component 108 and can be held in place when screws 110 are appropriately positioned. The mold 100 can be presented assembled and ready for cement injection to a user, such as a surgeon. The cement can be injected into the cavity 114 of the mold 100 through an injection port 112 formed from the first outer component 106 and the second outer component 108. Once injection is complete and the cement has cured, the screws 110 can be removed and the pull tabs 102 can be pulled in a direction away from the inner form block 104 to open the mold and release the cement femoral spacer 1000.

Figure 17:
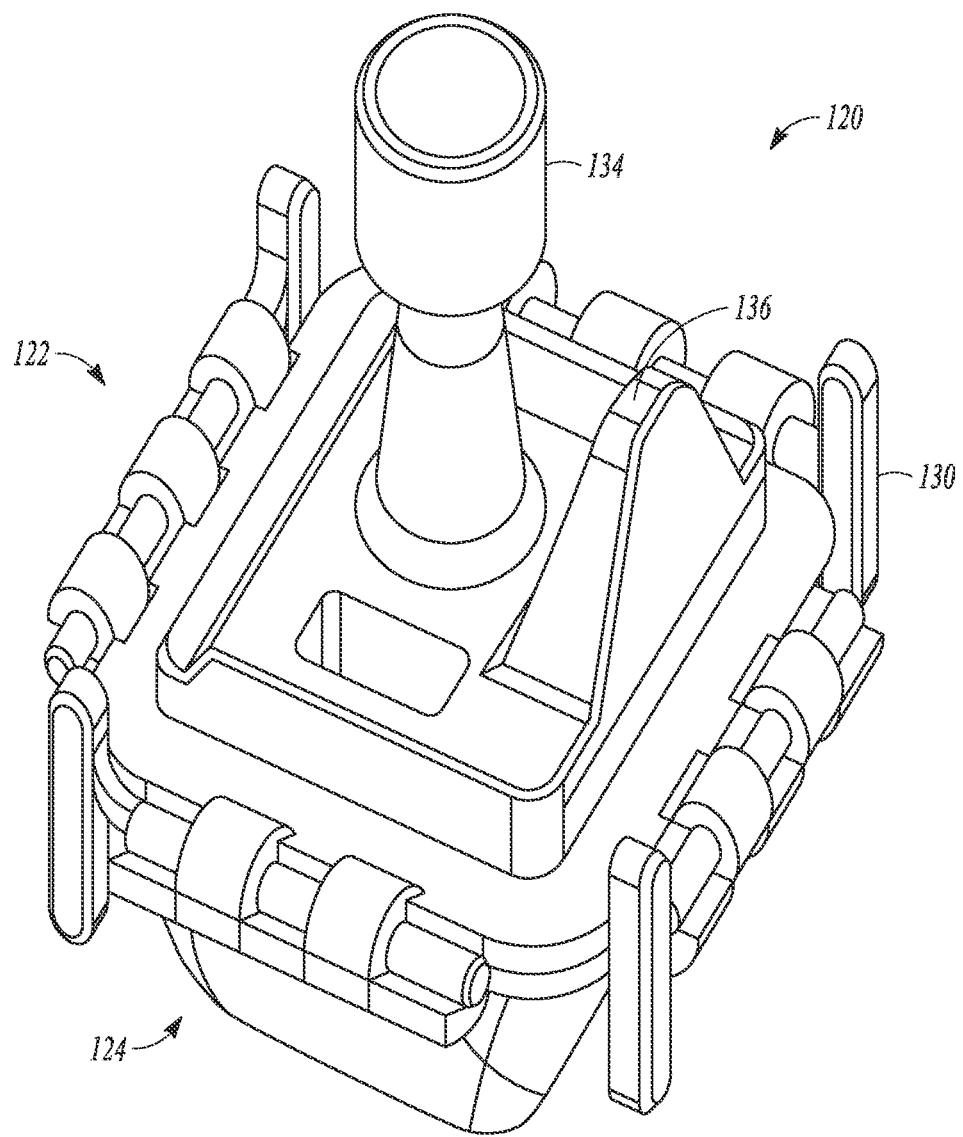
FIG. 17 is a perspective view of a direct-injection femoral mold according to the present disclosure.
Figure 18:
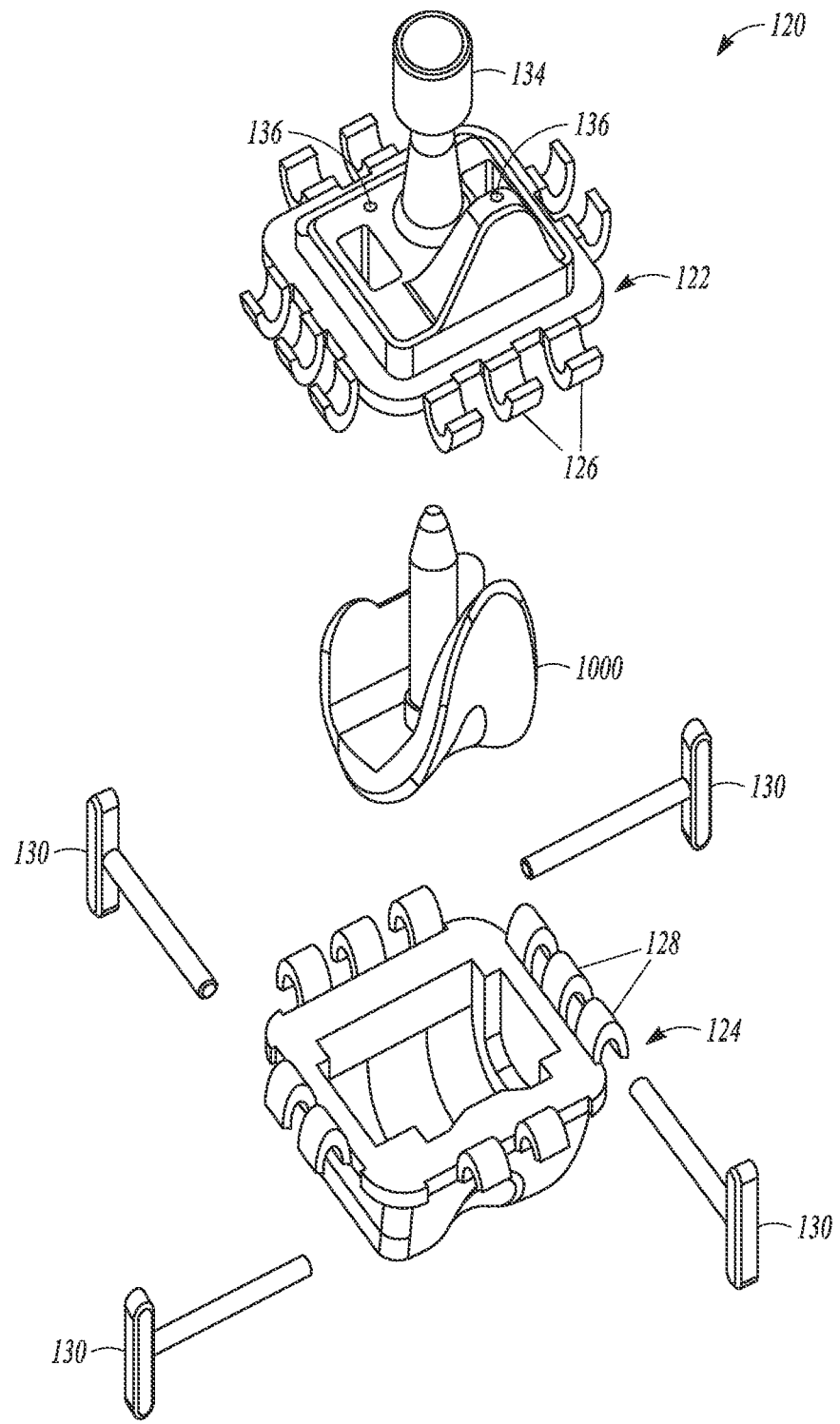
FIG. 18 is an exploded perspective view of the direct-injection femoral mold of FIG. 17.
Figure 19:
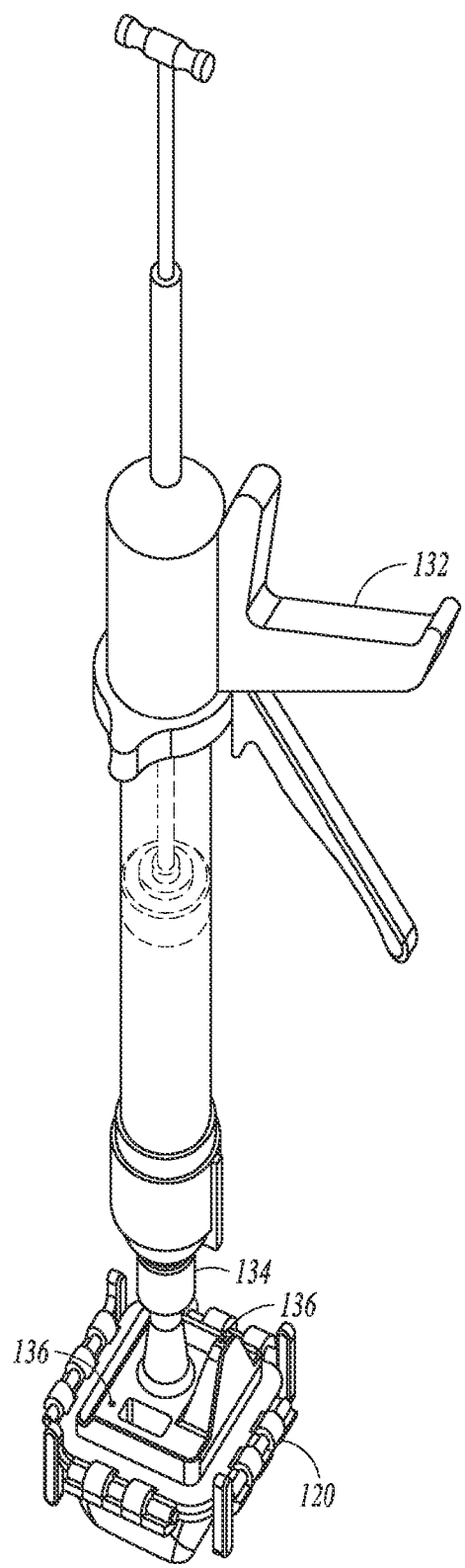
FIG. 19 is a perspective view of the direct-injection femoral mold of FIG. 17 attached to a cement injection gun.

FIGS. 17-19 illustrate another direct-injection femoral mold 120 according to the present disclosure. The mold 120 can include a top portion 122 and a bottom portion 124. The top portion 122 can include a plurality of upward-opening extensions 126. The bottom portion 124 can include a plurality of downward opening extensions 128. Pull pins 130 can be positioned between extensions 126, 128 to secure the top portion 122 to the bottom portion 124. The mold 120 can be presented assembled and ready for cement injection to a surgeon. Cement can be injected into the mold 120 by the cement gun 132 through an injector port 134. The mold 120 can include strategically placed vent holes 136 at the tips of the anterior flange 1006 and the posterior condyles 1008, 1010. During filling, once cement beings to exit vent holes 136, the mold 120 is full. Once the cement is injected and cured, pull pins 130 can be removed and the top portion 122 can be separated from the bottom portion 124 to remove the cured femoral spacer 1000.

Figures 20, 21:
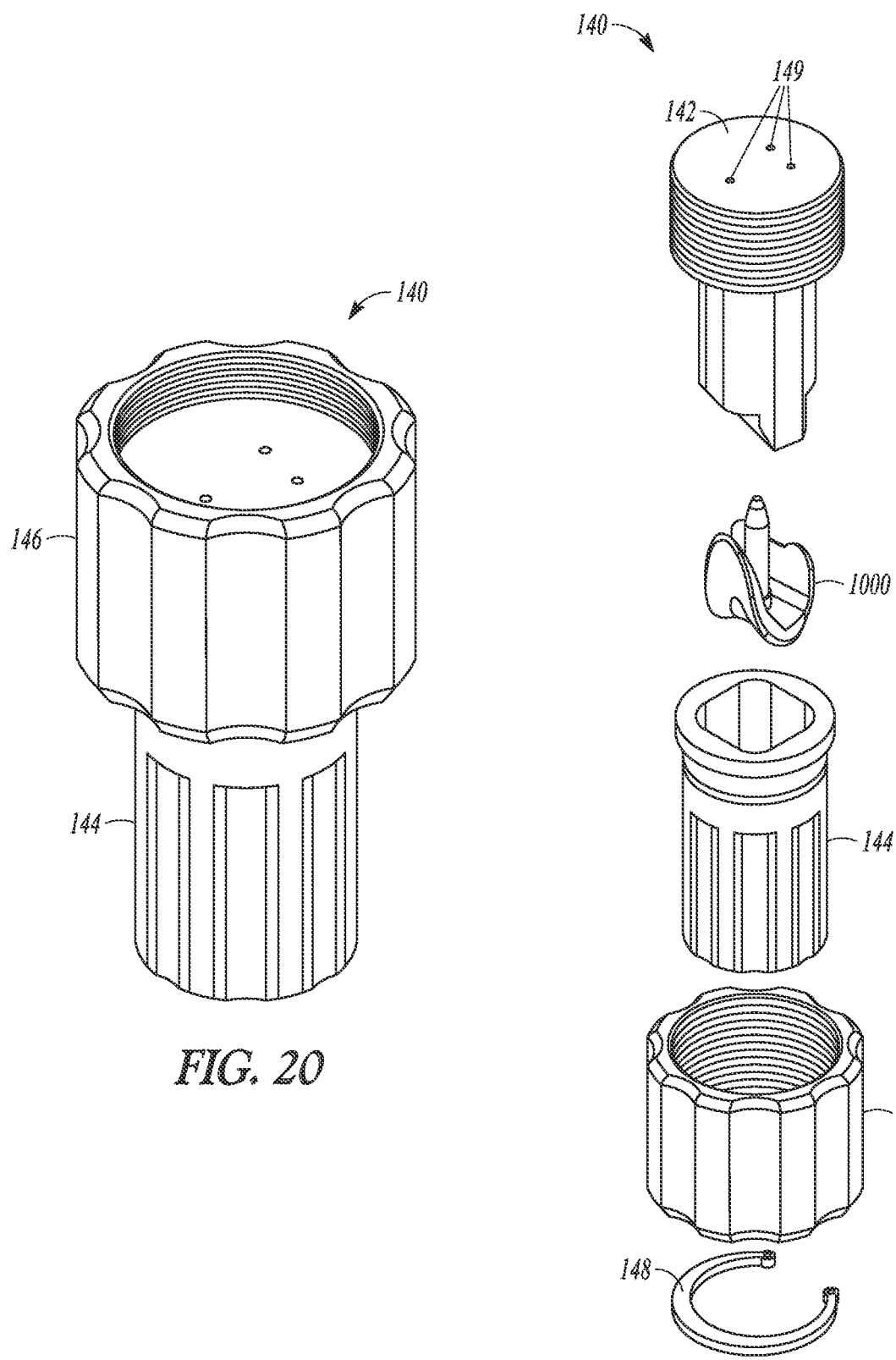
FIG. 20 is a perspective view of a femoral compression mold in accordance with the present disclosure.
FIG. 21 is an exploded perspective view of the femoral compression mold of FIG. 20.

FIGS. 20-21 illustrate a compression femoral mold 140. The compression femoral mold 140 can comprise a plunger 142, a cavity member 144, a lid 146, and a retaining ring 148. Bone cement can be mixed and placed into the cavity member 144 to a specified or predetermined fill line (not shown). The plunger 142 can be then inserted into the cavity member 144 and the lid 146, containing the retaining ring 148, can be screwed onto the plunger 142. As the lid 146 is screwed onto the plunger 142, the plunger 142 can be compressed down into the cavity member 144, forming a cement femoral spacer 1000. When the lid 146 is completely screwed onto the plunger 142, the cement femoral spacer 1000 can be fully formed. After the cement is cured, the lid 146 can be screwed off of the plunger 142. The retaining ring 148 in the lid 146 can grab the plunger 142 as the lid 146 is unscrewed, and, in so doing, removes the plunger 142 along with the lid 146. The cured cement femoral spacer 1000 can then be removed from the cavity member 144. During filling, once cement beings to exit vent holes 149, the mold 140 is full.

Figures 22, 23:
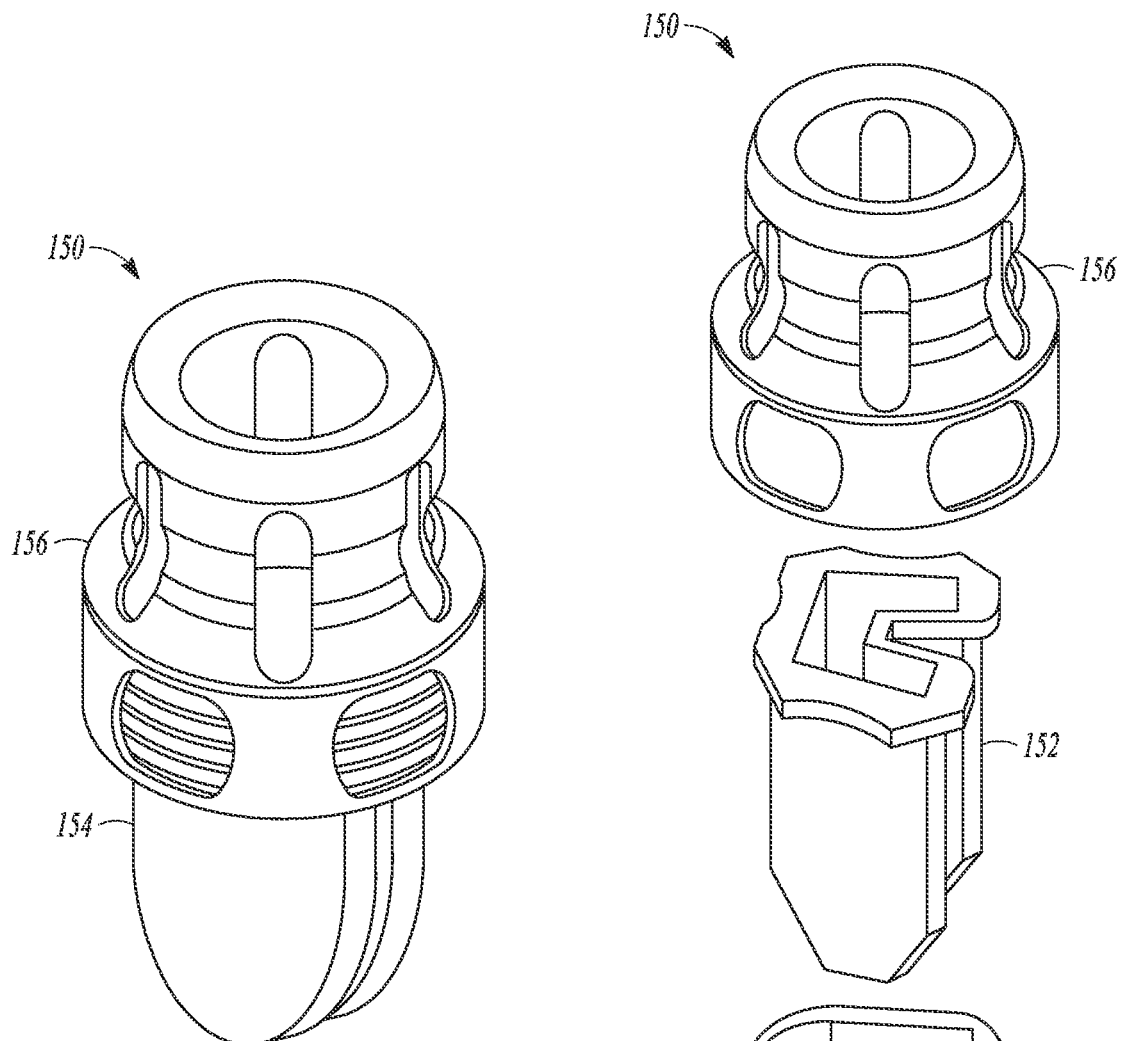
FIG. 22 is a perspective view of another femoral compression mold in accordance with the present disclosure.
FIG. 23 is an exploded perspective view of the femoral compression mold of FIG. 22.

FIGS. 22-23 illustrate another compression femoral mold 150. The compression femoral mold 150 can comprise a plunger 152, a cavity member 154, and a lid 156. Bone cement can be mixed and manually injected or otherwise placed into the cavity member 154 to a specified or predetermined fill line. The plunger 152 can then be inserted into the cavity member 144 and screwed into the lid 156 to compress the bone cement into a cement femoral spacer 1000 shape. A plurality of vents in the plunger 152 can allow excess cement to exit the cavity. The lid 156 can be snapped together with the plunger 152 to form an integral assembly. After the cement is cured, the lid 156 and the plunger 152 are removed and the cured cement femoral spacer 1000 can be removed from the cavity member 144.

Figure 24:
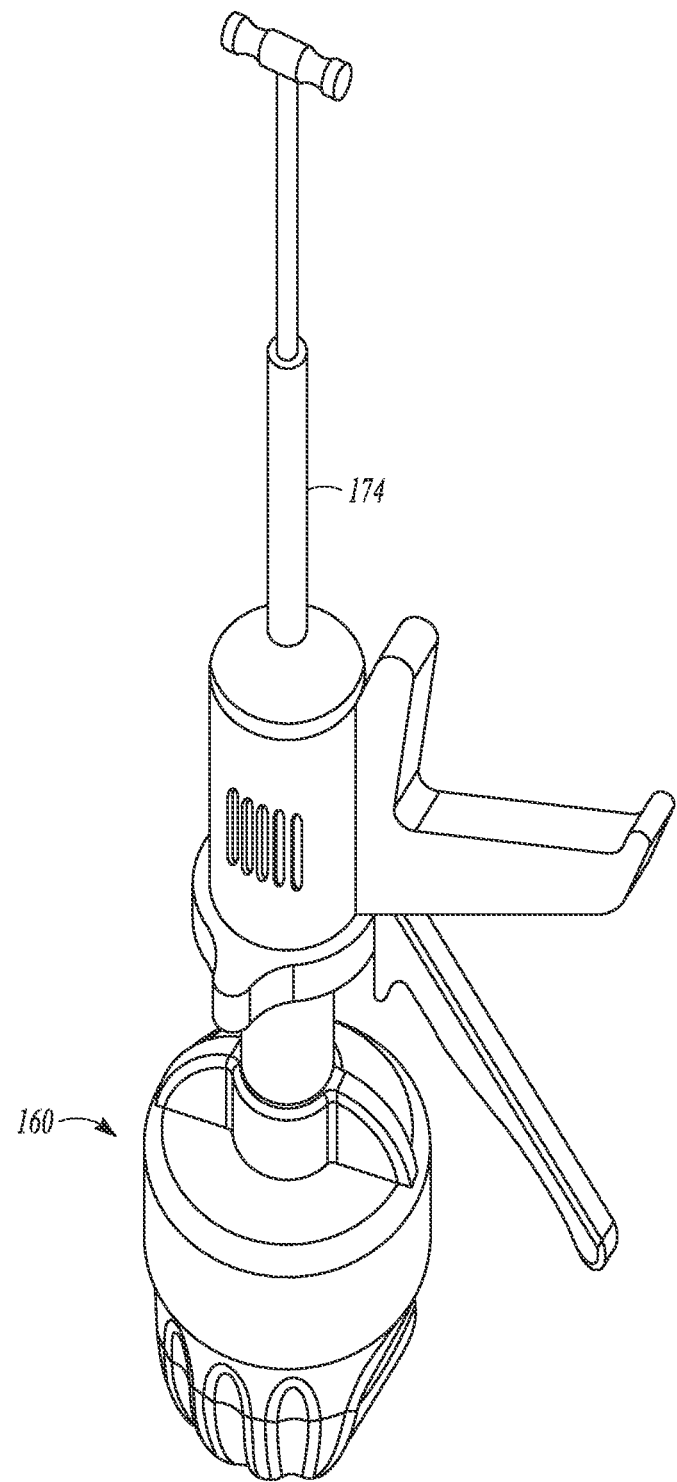
FIG. 24 is a perspective view of a femoral compression mold compressed with a cement gun in accordance with the present disclosure.
Figure 25:
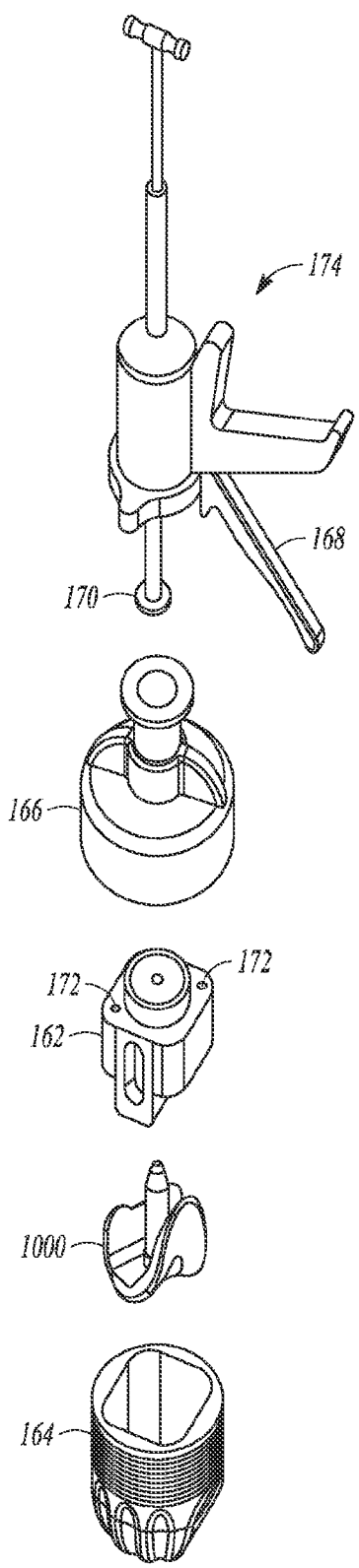
FIG. 25 is an exploded perspective view of the femoral compression mold and cement gun of FIG. 24.

FIGS. 24-25 illustrate a compression femoral mold 160 to be compressed with an attached cement gun 174. The compression femoral mold 160 comprises a plunger 162, a cavity member 164, and a lid 166. Bone cement can be mixed and manually injected into the cavity member 164 to a specified or predetermined fill line. The plunger 162 can be positioned above the cement, and the lid 166 can be screwed onto the cavity member 164. The cement gun 174, shown without a cement cartridge, can be attached to the top of the lid 166. A handle 168 of the cement gun 174 can be squeezed repeatedly, causing a compression rod 170 to apply pressure to the plunger 162, which will form the cement into a cement femoral spacer 1000 shape. The user will know when the mold is fully compressed when cement begins to exit out of vent holes 172 at the tips of the anterior flange 1006 and the posterior condyles 1008, 1010. Once the cement has cured, compression can be released by removing the cement gun 174. The lid 166 and the plunger 162 can be manually removed by unscrewing the lid 166 from the cavity member 164 to release the cement femoral spacer 1000.

Figure 26:
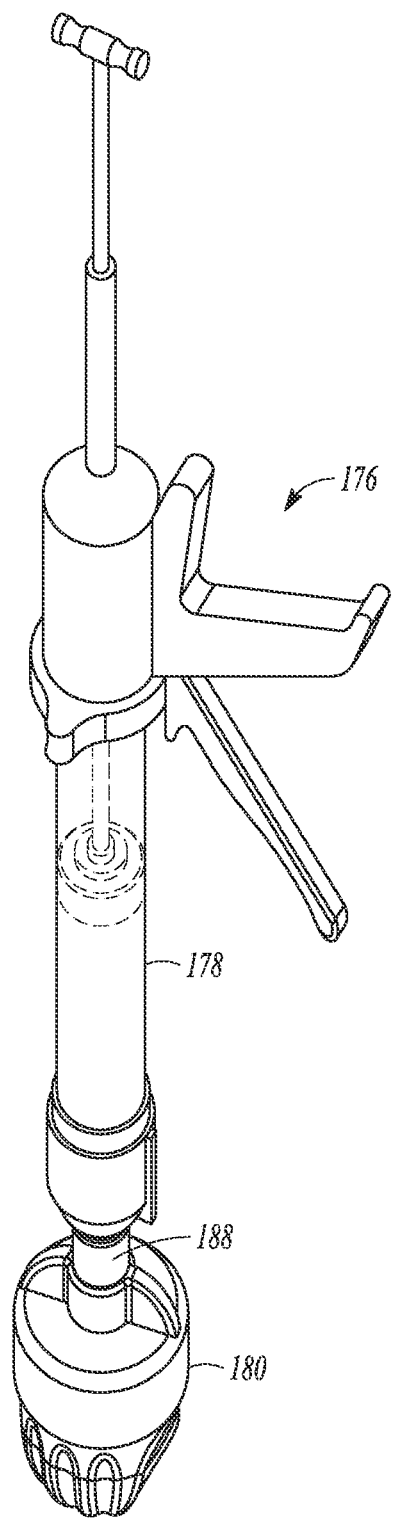
FIG. 26 is a perspective view of a femoral injection mold attached to a cement gun in accordance with the present disclosure.
Figures 27, 28:
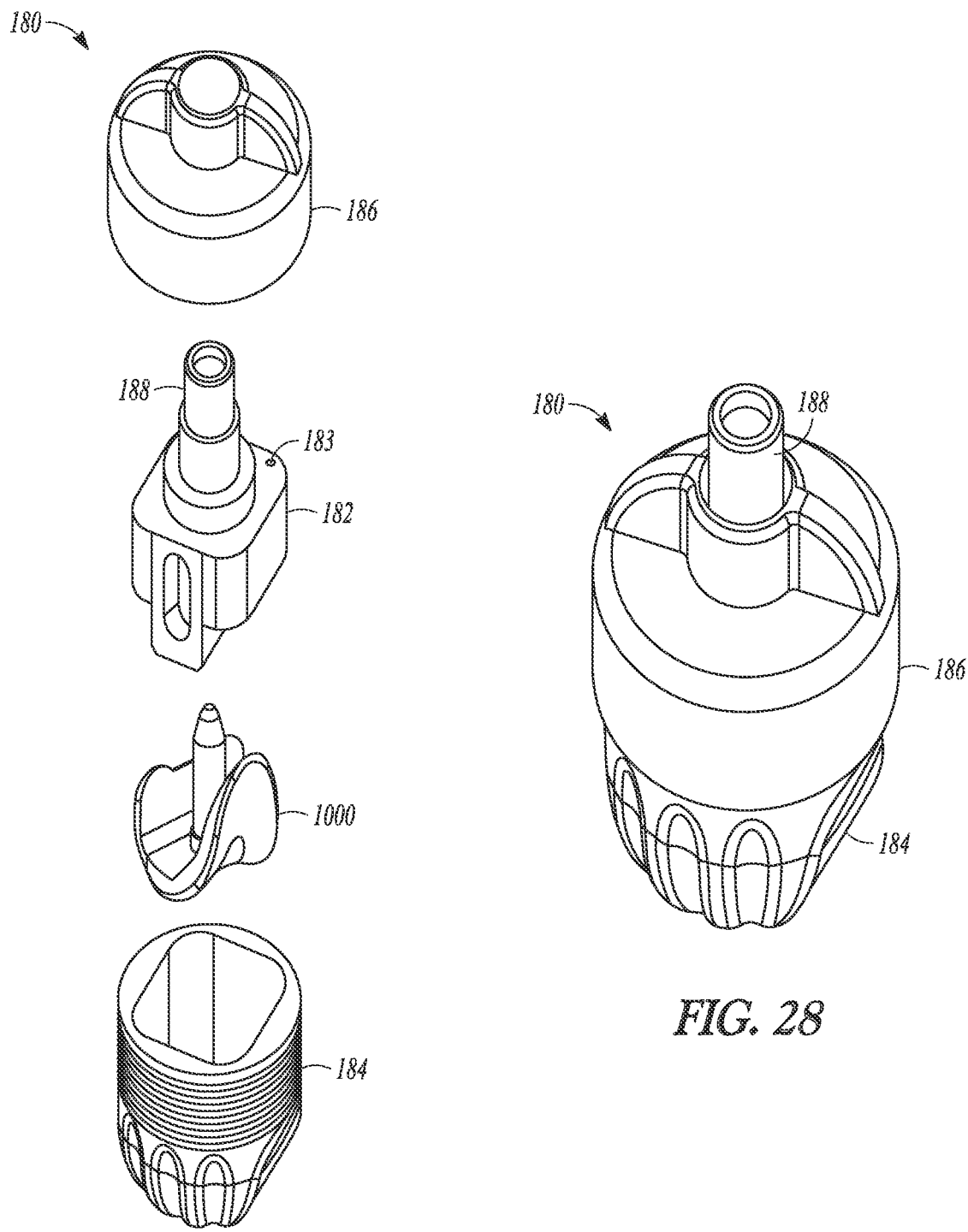
FIG. 27 is an exploded perspective view of the femoral injection mold of FIG. 26.
FIG. 28 is an assembled perspective view of the femoral injection mold of FIG. 27.

FIGS. 26-28 illustrate an injection femoral mold 180 attached to a cement gun 176 including a cement cartridge 178. The injection femoral mold 180 can be similar to the compression femoral mold 160, disclosed above, except the cement gun 176 includes the cement cartridge 178 to inject cement into the mold 180. The plunger 182 can be placed into a cavity member 184 and tightened into place by a screwing lid 186 onto the cavity member 184. The cement gun 176 can then be attached by a rigid connection to an injection port 188 on the lid 186, and cement can be injected into the mold 180. The user will know when the cement fully fills the mold when cement begins to exit out of vent holes 183 at the tips of the anterior flange 1006 and the posterior condyles 1008, 1010. Once the cement has cured, the lid 186 and the plunger 182 can be removed by unscrewing the lid 186 from the cavity member 184 to release a cement femoral spacer 1000.

Figure 29A:
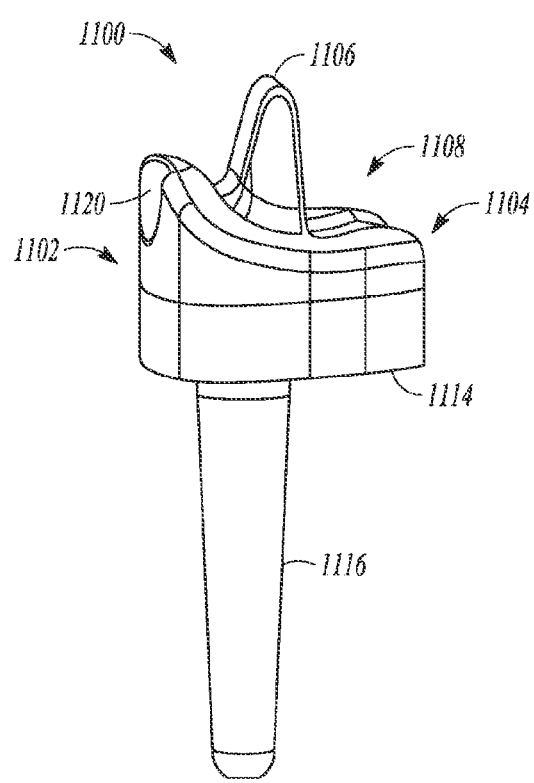
FIG. 29A is a perspective side view of a tibial spacer made in accordance with the present disclosure.
Figure 29B:
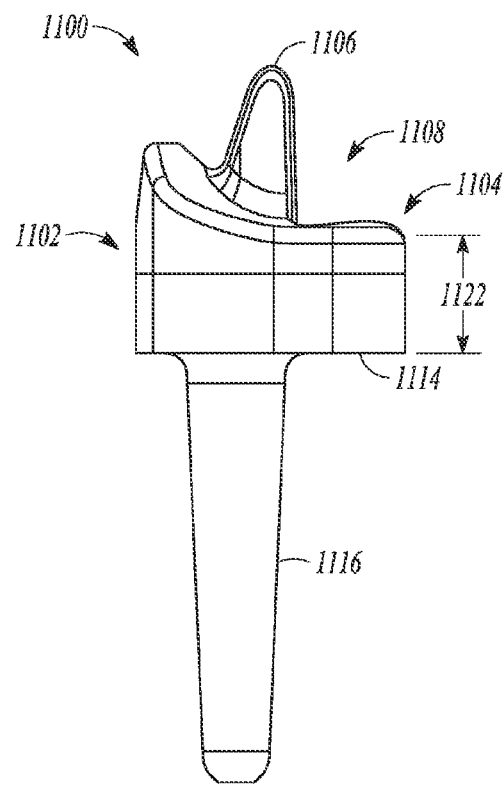
FIG. 29B is a side view of the tibial spacer of FIG. 29A.
Figure 29C:
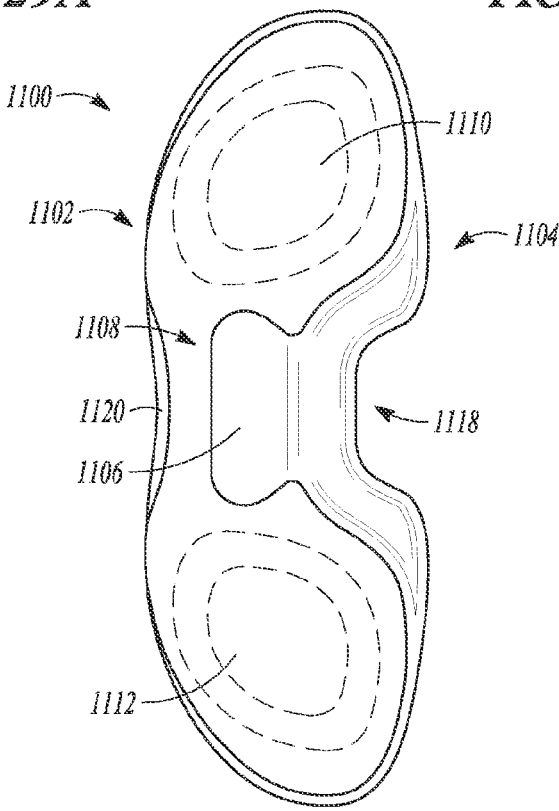
FIG. 29C is a top view of the tibial spacer of FIG. 29A.

Referring next to FIGS. 29A-29C, a tibial spacer 1100, formed from a tibial spacer mold 200 in accordance with the present disclosure, is illustrated. The tibial spacer 1100 can include an anterior edge 1102 and a posterior edge 1104. Disposed between the anterior edge 1102 and the posterior edge 1104 can be a spine 1106. An articulating surface 1108 can include a lateral dished articular component 1110 and a medial dished articular component 1112. The dished articular components 1110, 1112 can be sized, shaped, and positioned to cooperate with the medial posterior condyle 1008 and the lateral posterior condyle 1010 of the femoral spacer 1000 (FIG. 1).

The tibial spacer 1100 can further include a distal surface 1114, opposite articulating surface 1108, which includes an intermedullary post 1116 for insertion into patient bone to stabilize and secure the tibial spacer 1100. A posterior cutout 1118 and anterior relief space 1120 can also be present in the tibial spacer 1100. A thickness 1122 is the distance between the low point in the dished articular components 1110, 1112, of the articulating surface 1108 and the bottom flat surface of the distal surface 1114. Other exemplary tibial prostheses are disclosed in U.S. Patent Publication No. 2010/0102484, the disclosure of which is hereby incorporated by reference in its entirety.

Figure 30:
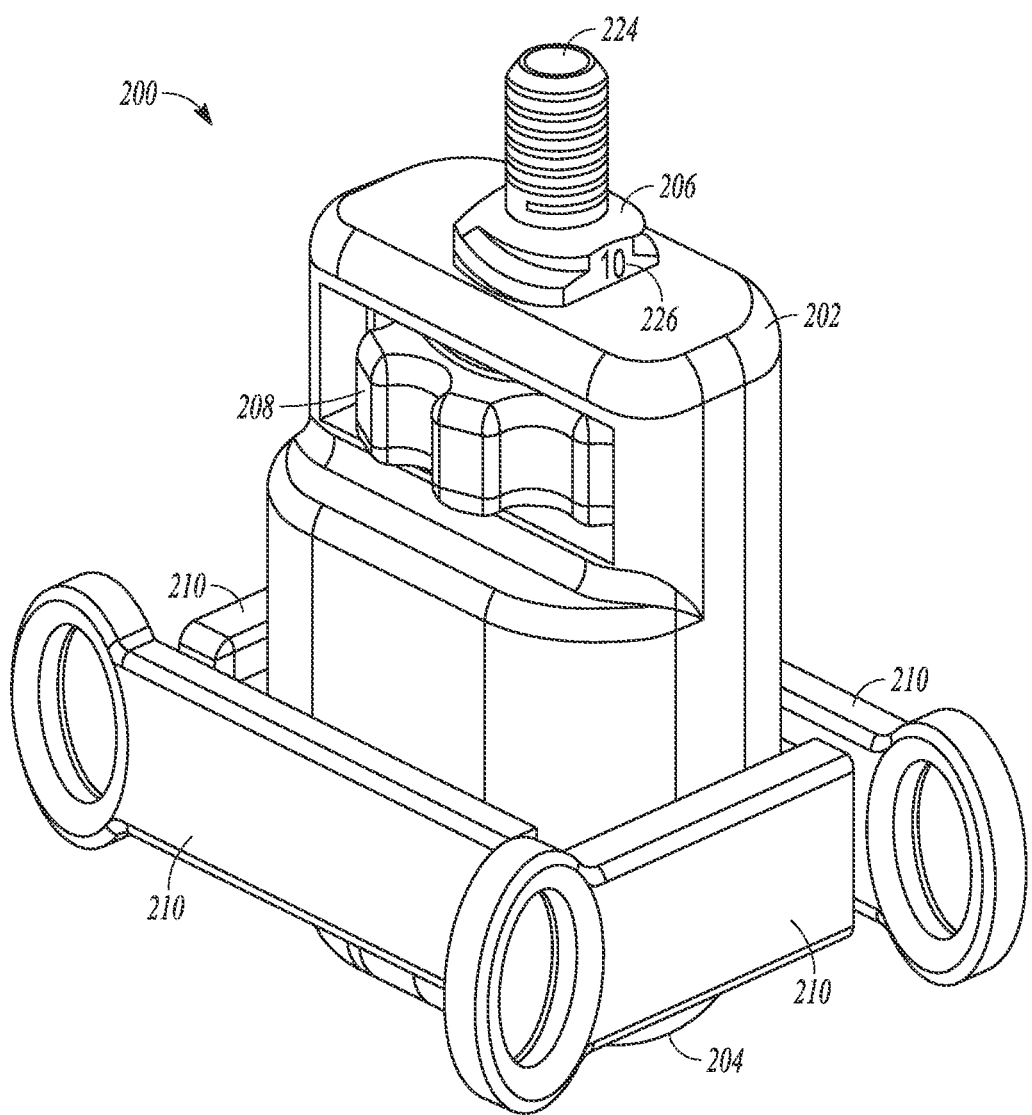
FIG. 30 is a perspective view of a tibial spacer mold in accordance with the present disclosure.
Figure 31:
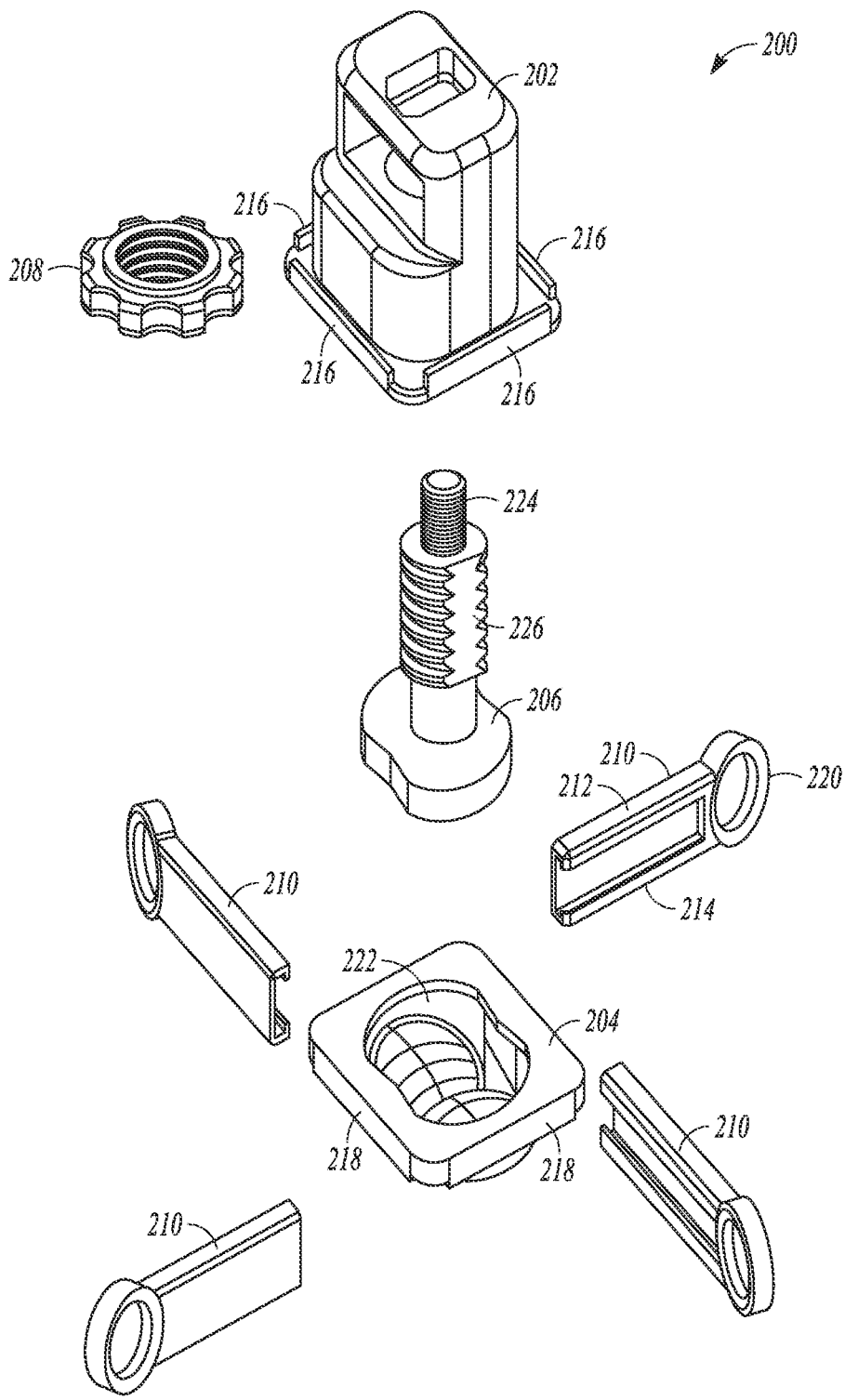
FIG. 31 is an exploded view of the tibial spacer mold of FIG. 30.
Figure 32:
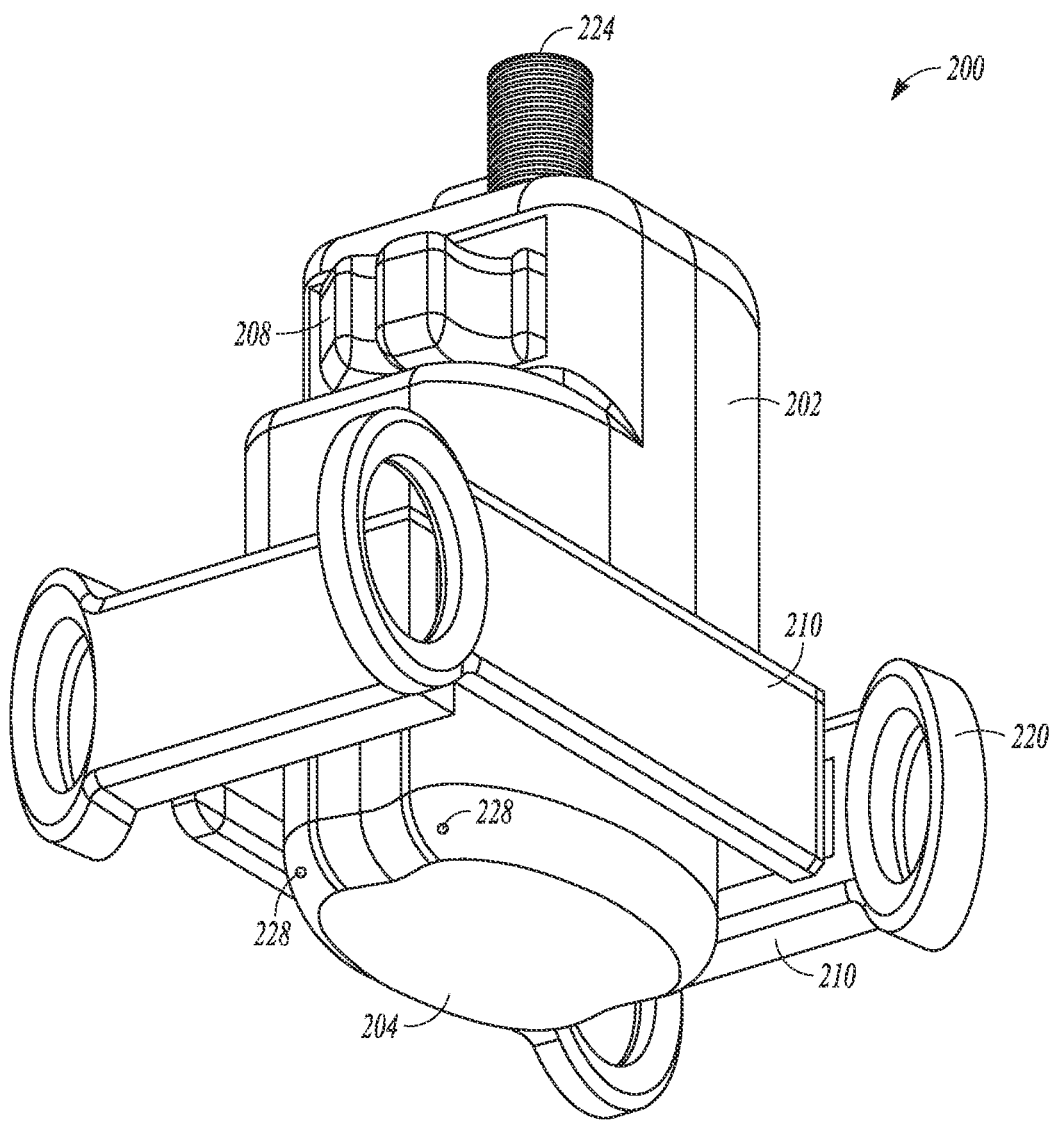
FIG. 32 is a bottom perspective view of the tibial spacer mold of FIG. 30.

Referring next to FIGS. 30-32, a tibial spacer mold 200, in accordance with the present disclosure, is illustrated. The tibial spacer mold 200 can be presented to a surgeon fully assembled and ready for cement injection. The tibial spacer mold 200 can comprise a top portion 202, a bottom portion 204, a plunger 206, an adjustment dial 208, and a plurality of locking members 210. As illustrated, the locking members 210 can be a plurality of C-channel-locking members. Other suitable numbers and types of locking members 210 can also be used.

As illustrated in FIGS. 30-32, the locking members 210 can each include a top edge 212 and a bottom edge 214. The top edge 212 can fit around a lip 216 on the top portion 202. The bottom edge 214 can fit around a lip 218 on the bottom portion 204. When the top portion 202 and the bottom portion 204 are assembled as in FIG. 28, the top edge 212 and the bottom edge 214 of locking members 210 can cooperate to secure the top portion 202 and the bottom portion 204. The locking members 210 can also include a grip 220 to allow easy movement of the locking members 210. As illustrated, the grip 220 can be a ring formed on one end of the locking members 210, but other suitable grips may also be used. As illustrated, the locking members 210 and the bottom portion 204 can cooperate to form a plurality of points along a plane. The tibial spacer mold 200 can rest on this plane in an upright orientation during cement injection and curing.

The plunger 206 can be moveably positioned in an interior of the top portion 202. The adjustment dial 208 can control the position of the plunger 206 within the top portion 202. In one form, the exterior surface of the plunger 206 and the interior surface of the adjustment dial 208 can include cooperating threaded surfaces, and turning the adjustment dial 208 can adjust the relative height of the plunger 206 within the tibial spacer mold 200. Adjusting the relative height of the plunger 206 can adjust the thickness of the tibial spacer 1100 formed from the tibial spacer mold 200. Specifically, adjusting the plunger 206 can adjust the thickness 1122 of the tibial spacer 1100.

A cavity 222 can be defined in a space between the plunger 206 and the bottom portion 204 of the mold 200, when assembled. An injection port 224 can provide access to the cavity 222 of the tibial spacer mold 200 to receive cement injected from a cement gun or other injector of pressurized, curable material. Cement can be provided from a cartridge of a cement gun at a pressure sufficient to spread the cement to substantially fill the interior of the tibial spacer mold 200. Specifically, the cement can fill the entirety of the cavity 222 from the injection port 224 forming the tibial spacer 1100 (FIG. 29), and the intermedullary post 1116 can be formed in the portion of the cavity interior to the plunger 206. The injection port 224 can be axially aligned with the formed intermedullary post 1116.

The injection port 224 and the remainder of the tibial spacer mold 200 can have sufficient rigidity to receive the cement under high pressure, without compromising the connection between the injection port 224 and the cement source or breaking, splitting, or cracking the tibial spacer mold 200 when the pressurized cement is received under pressure. For these purposes, in one form, high density polyethylene can be used to form the tibial spacer mold 200. In one form, cement can be received directly into the injection port 224. In another form, cement may not be received directly into the injection port 224, but instead through an adaptor plug. The adaptor plug can be similar or identical to the adaptor plug 32 (FIG. 3).

The plunger 206 can include a tibial thickness indicator 226. The tibial thickness indicator can display a corresponding thickness of the tibial spacer 1100 formed by the tibial spacer mold 200, based, at least in part, on a position of the plunger 206. In an exemplary form, the tibial thickness indicator can be marked to vary the thickness 1122 between about 10 mm and about 30 mm. The thickness can be adjusted to properly balance the flexion and extension gaps of the knee upon implantation.

As shown in FIG. 32, the tibial spacer mold 200 can include strategically placed vent holes 228 communicating with the cavity 222 at positions corresponding to the tips of the tibial spacer 1100 around the posterior cutout 1118 (FIG. 29). During filling, once cement beings to exit vent holes 228, the tibial spacer mold 200 is full. The cement gun and adaptor plug can be removed. A cleaning plug can then be used to clear excess cement from the injection area before the cement cures and becomes stuck to the tibial spacer 1100. The cleaning plug can be similar or identical to the cleaning plug 42 (FIG. 3).

Referring again to FIGS. 30-32, once the cement has fully cured, the locking members 210 can be removed by sliding them off of the lips 216, 218. The cleaning plug can be removed from the injection port 224. The adjustment dial 208 can then be turned to move the plunger 206 downward, forcing the mold 200 apart and releasing the tibial spacer 1100 from mold 200.

Figure 33:
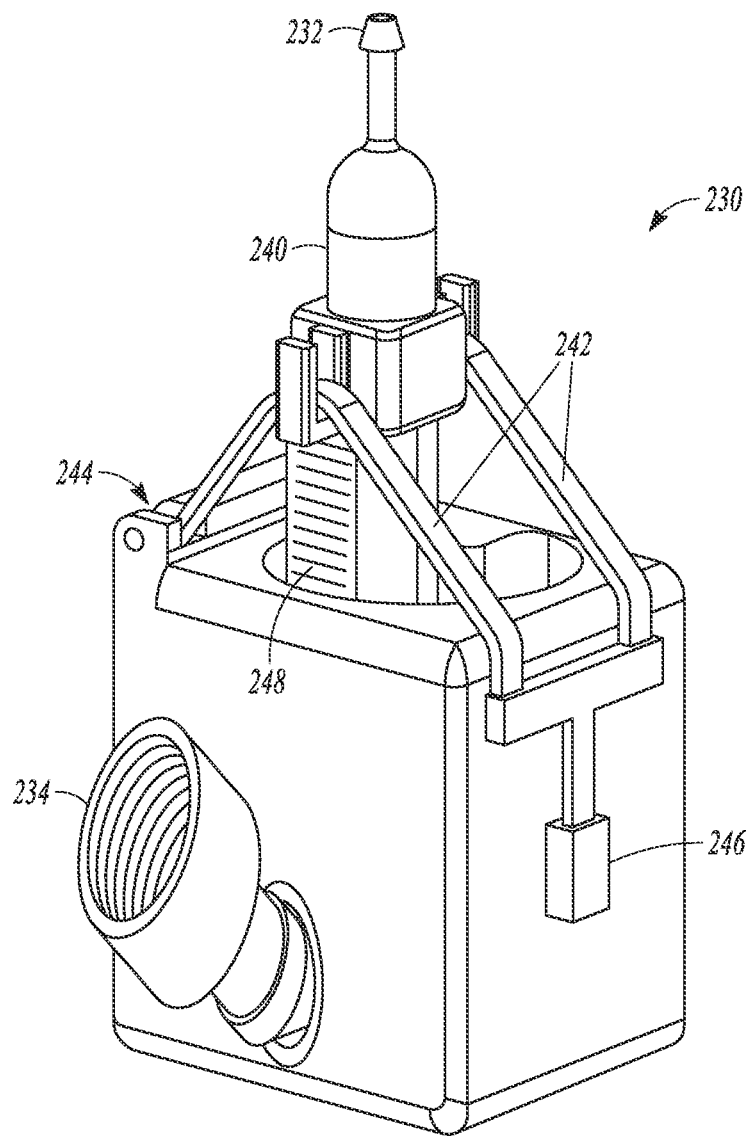
FIG. 33 is a perspective view of a tibial insert mold including a vacuum connection in accordance with the present disclosure.
Figure 34:
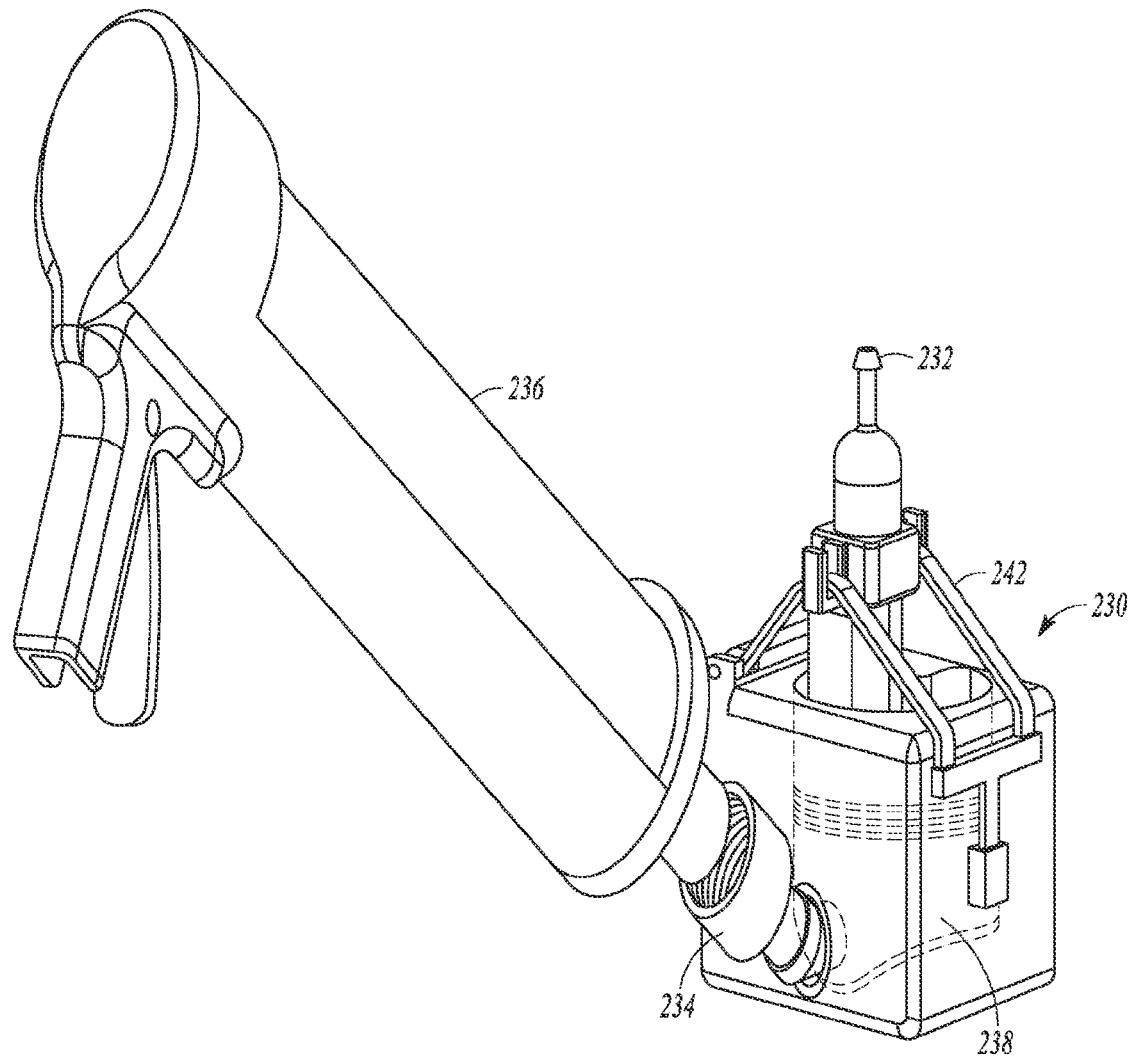
FIG. 34 is a perspective view of the tibial insert mold of FIG. 33 attached to a cement injection gun.

Referring next to FIGS. 33-34, a tibial insert mold 230 including a vacuum connection 232 is illustrated. The mold 230 can include a rigid threaded connection 234, into which cement can be injected from a cement gun 236. A standard vacuum tube can be connected to the vacuum connection 232. The vacuum connection can be fluidly connected to a cavity 238 in the mold 230. A vacuum can be applied to the cavity 238 through the vacuum connection 232, aiding in complete and rapid filling of the mold 230. The vacuum aids in filling the mold 230 easily and without significant voids or air pockets.

The mold 230 can include a plunger 240 forming one side of the cavity 238. The plunger 240 can be moveable within the mold 230, allowing for different thicknesses 1122 of the formed tibial spacer 1100. An upper limit to the plunger 240 movement can be provided using rigid straps 242. One end 244 of a rigid strap 242 is fixed, while another end is attached to a locking mechanism 246 on a side of the mold 230. In one form, the end 244 can include serrated edges, and the locking mechanism 246 can allow the end 244 to be moved in one direction but not the opposite direction. In this way, as cement fills the cavity 238, the plunger 240 can be forced upward until it contacts the rigid straps 242. A face of the plunger 240 or the locking mechanism 246 can include a display 248, which indicates to the user the thickness 1122 of the tibial spacer 1100 produced. After the cement has cured, the locking mechanism 246 can be released, and the plunger 240 and the tibial spacer 1100 can be removed from the cavity 238.

Figure 35:
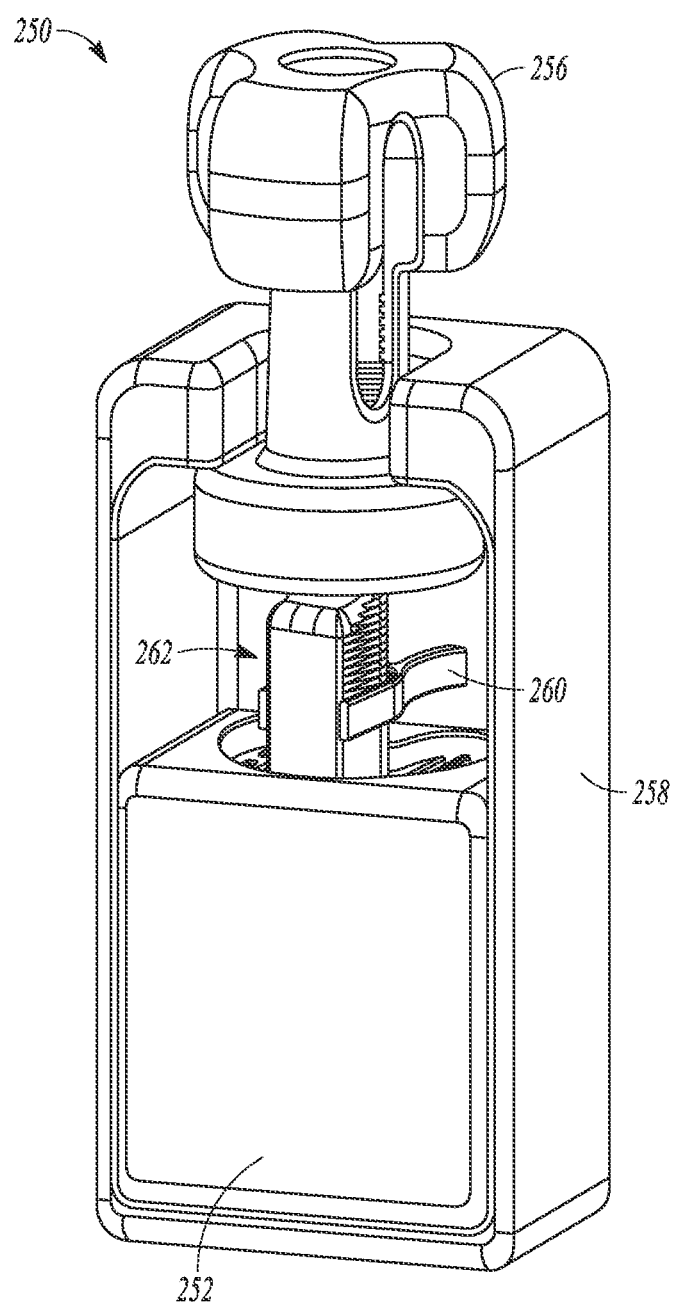
FIG. 35 is a perspective view of a tibial insert compression mold including an adjustable clip in accordance with the present disclosure.
Figure 36:
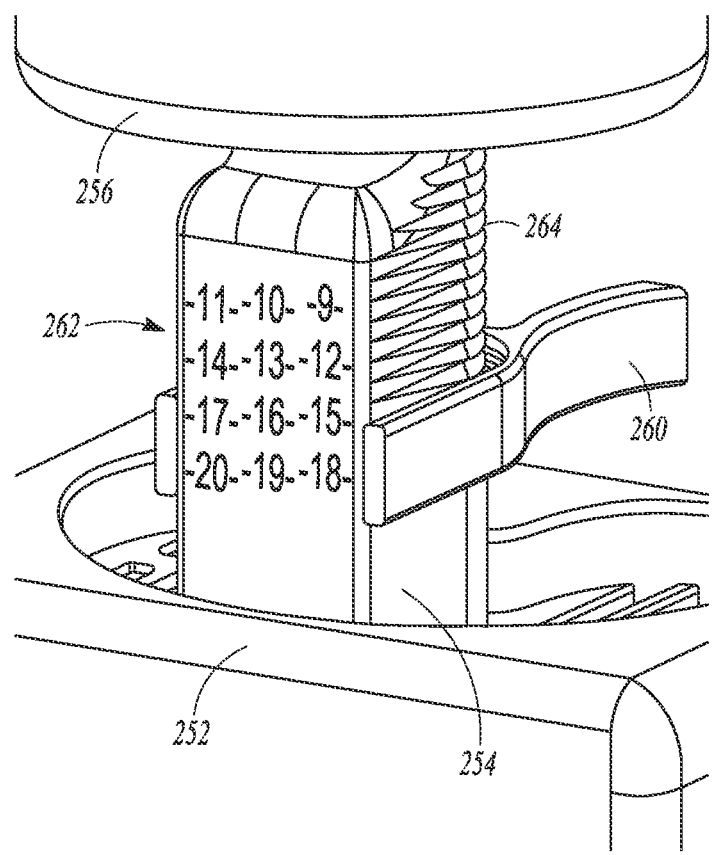
FIG. 36 is a view of the clip and level indicator of the tibial insert compression mold of FIG. 35.
Figure 37:
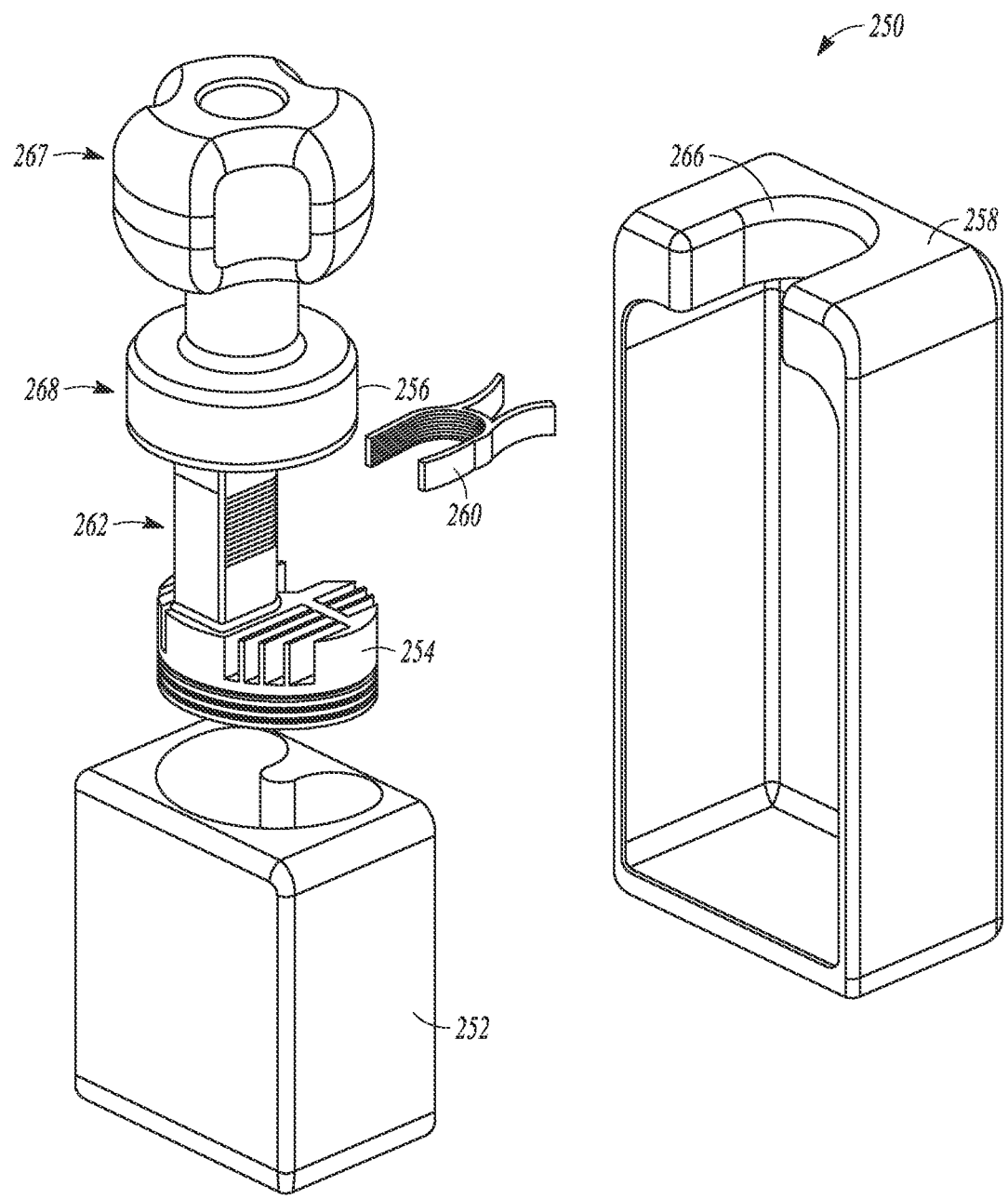
FIG. 37 is an exploded view of the tibial insert compression mold of FIG. 35.

Referring next to FIGS. 35-37, a compression tibial insert mold 250 is illustrated. The mold 250 can include a cavity member 252, a plunger 254, a handle 256, a housing 258, and a clip 260.

The cavity member 252 can be manually filled with bone cement up to an indicated fill line depending on a desired thickness 1122 of a tibial spacer 1100. The clip 260 can be attached at the desired thickness of a display 262 on one face of the plunger 254. The display 262 can indicate to the user how thick 1104 the tibial spacer 1100 produced will be. The plunger 254 can include a plurality of clip levels 264 corresponding to the thickness 1122 of the formed tibial spacer 1100.

The plunger 254 can be inserted into the cavity member 252 and the plunger 254 and the cavity member 252 can be placed in the housing 258. The housing 258 can include a recess 266, through which a top portion 267 of the handle 256 extends, while a lower portion 268 of handle 256, that is wider than the recess 266, does not. The plunger 254 can then be compressed downward by rotating the handle 256 to compress the cement into a proper shape for the tibial spacer 1100. The housing 258 can provide a counter-force for the lower portion 268 of the handle 256 while the plunger 254 can be screwed downward. The clip 260 can contact the top surface of the cavity member 252, stopping the downward movement of the plunger 254. A vent hole in the plunger 254, at the tip of the intermedullary post 1116 of the tibial spacer 1100, can allow excess cement to exit, indicating the fullness of the mold 250. After the cement has cured, the handle 256 can be rotated in the opposite direction, releasing the force on the plunger 254. The cavity member 252 can be removed from the housing 258, and the plunger 254 and the tibial spacer 1100 can be removed.

Figure 38:
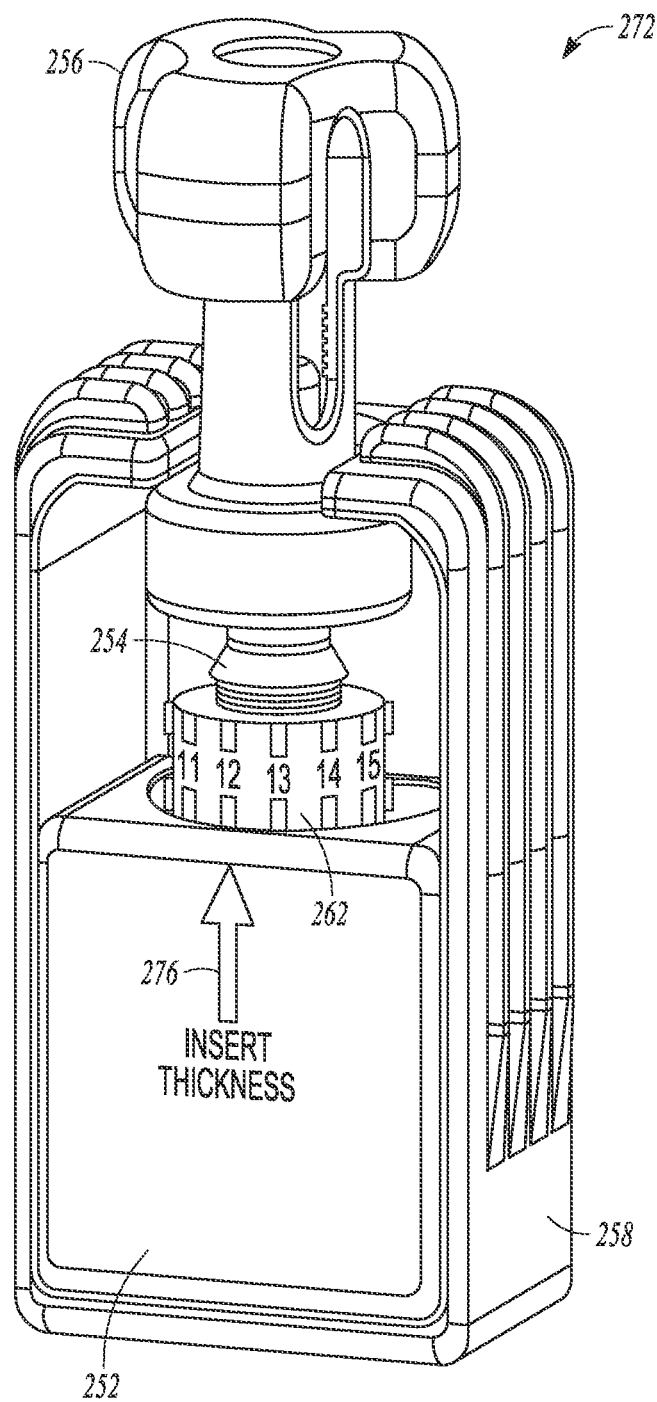
FIG. 38 is a perspective view of another tibial insert compression mold in accordance with the present disclosure.
Figure 39:
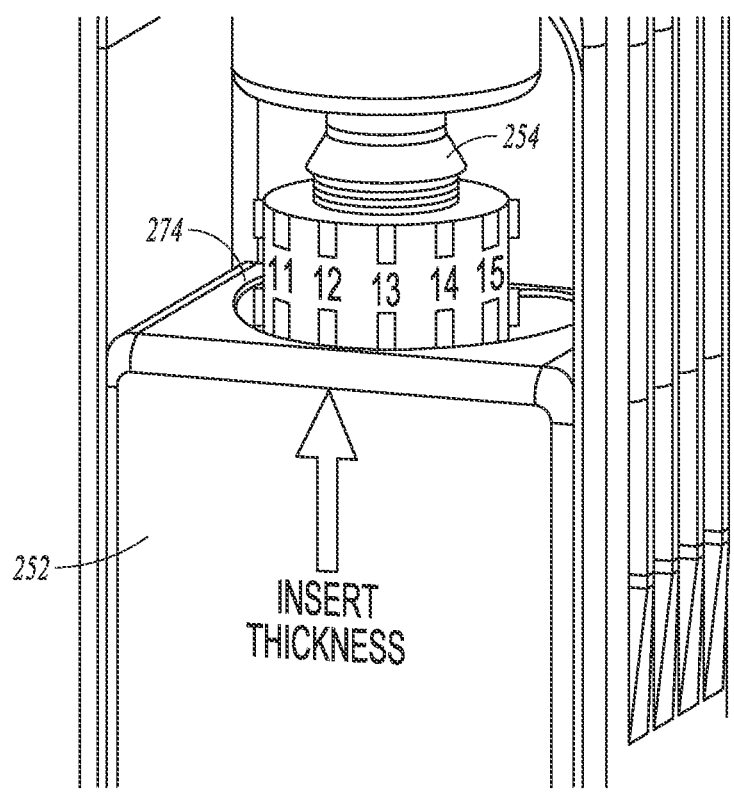
FIG. 39 is a view of the dial indicator of the tibial insert compression mold of FIG. 38.

Referring next to FIGS. 38-39, another compression tibial insert mold 272 is illustrated. The compression tibial insert mold 272 can be similar to the mold 250 disclosed above, except that the clip 260 and the clip levels 264 on the mold 250 can be replaced by an adjustment dial 274 on the mold 272. The adjustment dial 274 can display numbers corresponding to a thickness 1122 of a tibial insert produced. The adjustment dial 274 and the plunger 254 can include cooperating threaded surfaces, such that as the adjustment dial 274 is rotated, the plunger 254 can be moved up or down within the cavity member 252. The cavity member 252 or the housing 258 can include a display indicator 276 in line with the corresponding thickness on the adjustment dial 274.

Figure 40:
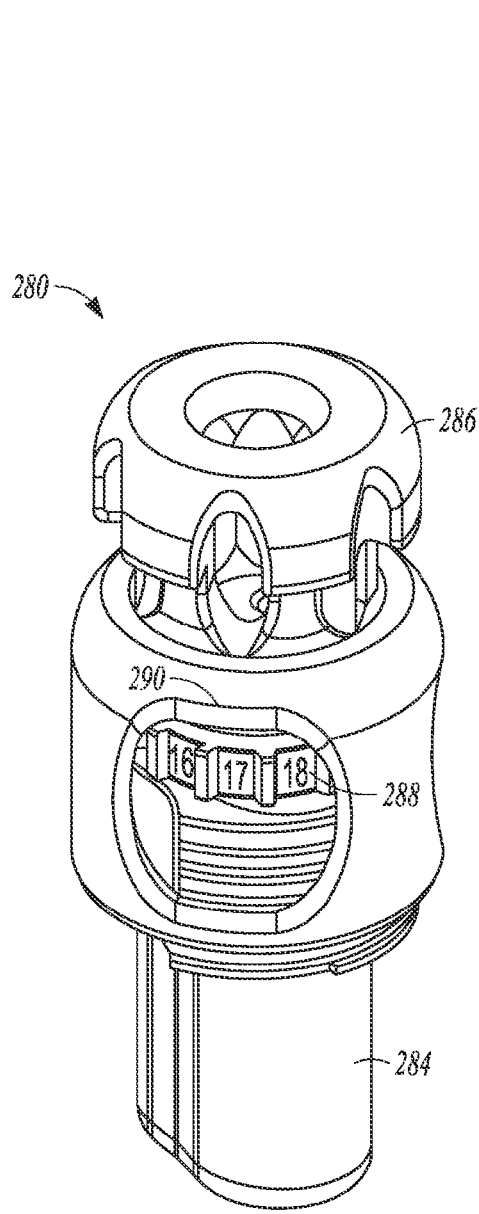
FIG. 40 is a perspective view of a tibial compression mold in accordance with the present disclosure.
Figure 41:
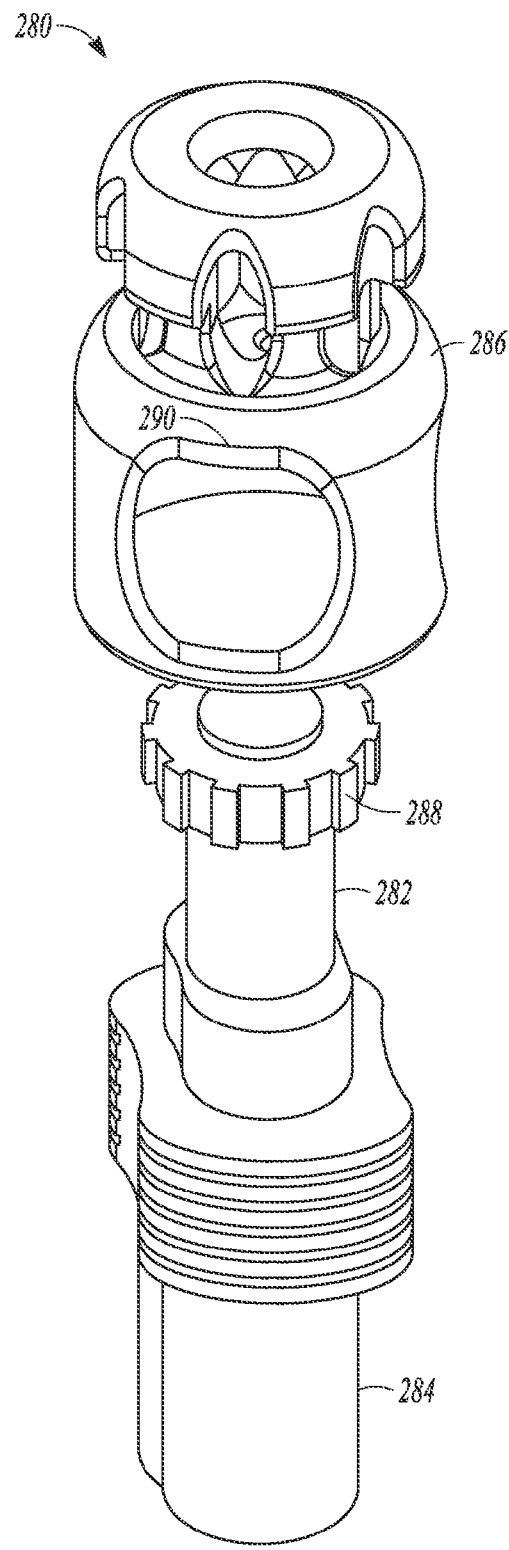
FIG. 41 is an exploded view of the tibial compression mold of FIG. 40.

Referring next to FIGS. 40-41, still another compression tibial insert mold 280 is illustrated. The compression tibial insert mold 280 can comprise a plunger 282, a cavity member 284, and a lid 286. Bone cement can be mixed and manually injected into the cavity member 284 to a specified or predetermined fill line. A desired thickness 1122 of a tibial spacer 1100 can be selected from an adjustment dial 288 connected to the plunger 282. The lid 286 can include a display indicator 290 in line with the corresponding thickness of the adjustment dial 288. The plunger 282 can then be inserted into the cavity member 284 and screwed into the lid 286 to compress the bone cement into the tibial spacer 1100 shape. The adjustment dial 288 can control how far the cavity member 284 can be screwed into the lid 286. The adjustment dial 288 and the plunger 282 can have cooperating threaded surfaces such that as the adjustment dial is rotated, more or less of the cavity member 284 can be screwed into the lid 286. After the cement is cured, the lid 286 can be snapped together with the plunger 282 to form an integral assembly. The lid 286 and the plunger 282 assembly can then be removed and the cured cement tibial spacer 1100 can be removed from the cavity member 284.

Figure 42:
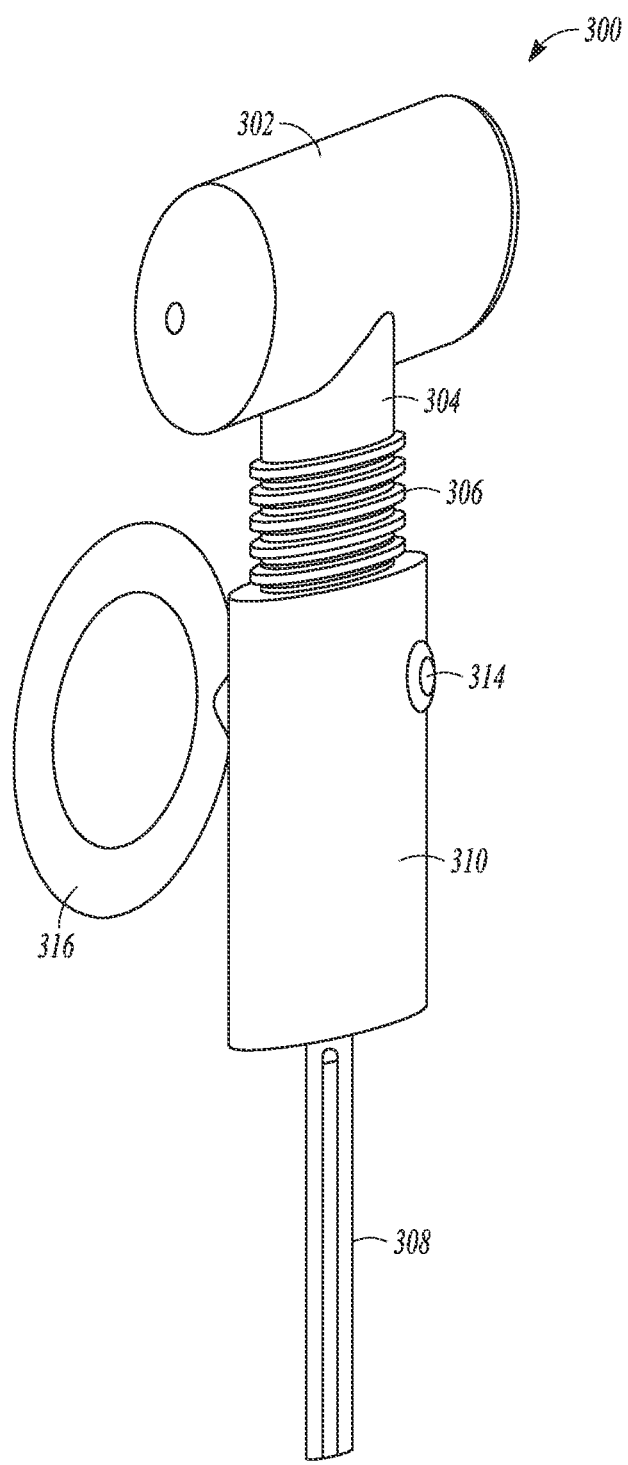
FIG. 42 is a side view of a cleaning/injection plug for direct injection molds in accordance with the present disclosure.
Figure 43:
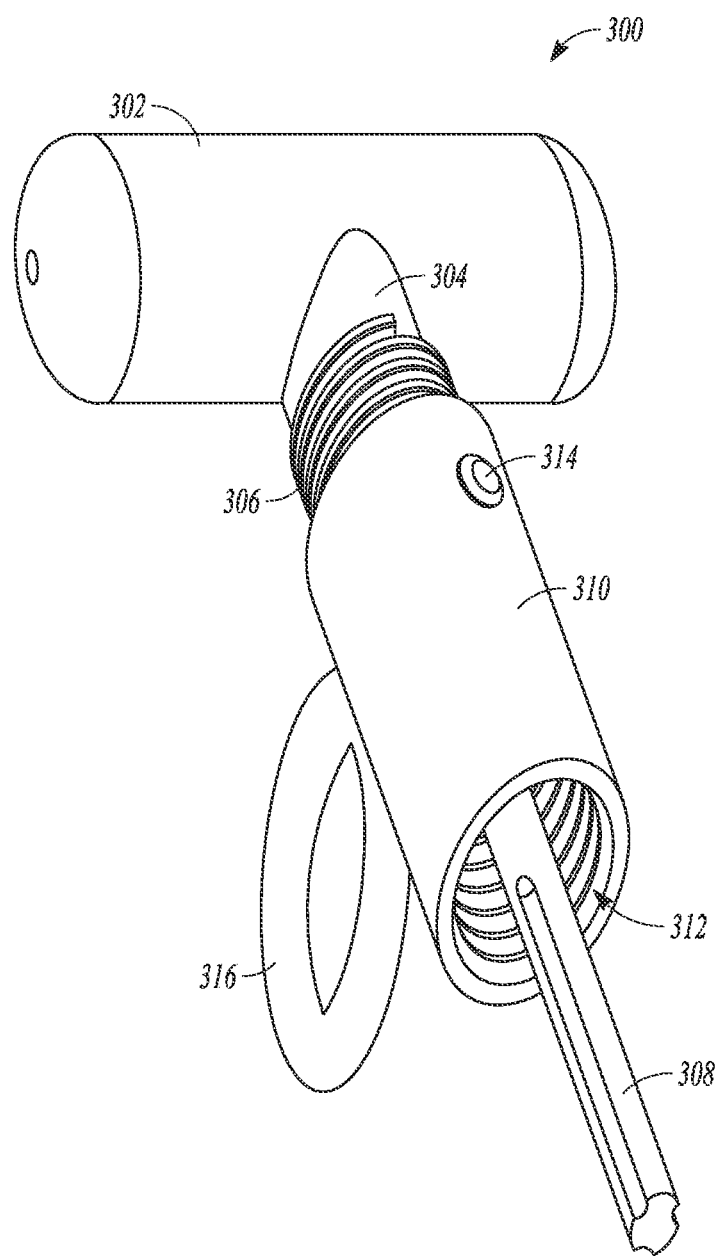
FIG. 43 is a bottom perspective view of the cleaning/injection plug of FIG. 42.

Referring next to FIGS. 42-43, a cleaning/injection plug 300 is illustrated. The plug 300 can be used with injection molds, such as those disclosed above. The plug 300 can combine cleaning plugs, such as the cleaning plug 42 disclosed above, and ejection plugs, such as the ejection plug 46 disclosed above. One end of the plug 300 can be formed into a T-handle 302. The T-handle 302 can be attached to the threaded portion 304, which can include external threads 306 on its surface. The opposite end of the plug 300 can include the stem 308. An annular element 310, having an internal threaded surface 312, can be attached to external threads 306 of the threaded portion 304. Once an injection mold is injected with cement, the internal threaded surface 312 of the annular element 310 can be screwed onto an adaptor plug, such as those previously described, by rotating the T-handle 302. As the plug 300 is screwed onto an adaptor plug, excess cement can be cleaned out of the area. The T-handle 302 can be rotated until the cross-pin 314 prevents further rotation. In this way, the plug 300 can be used as a cleaning plug, as described above for the cleaning plug 42.

Once the cement is fully cured and the cement spacer is ready to be ejected, a cross-pin 314 can be removed by pulling on a cross-pin handle 316, and the T-handle 302 can again be rotated, applying pressure to the cured femoral spacer 1000 and separating portions of the mold. In this way, the plug 300 can be used as an ejection plug, as described above for the ejection plug 46. Use of a single plug 300 can eliminate the need for separate components and can simplify the use of the mold for the customer.

The above Detailed Description includes references to the accompanying drawings, which form a part of the Detailed Description. The drawings show, by way of illustration, specific embodiments in which a handle assembly and related methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In the event of inconsistent usages between this document and any document so incorporated by reference, the usage in this document controls.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "having," "including" and "in which" are used as the plain-English equivalents of the respective terms "comprising" and "wherein." The terms "having", "including" and "comprising" are open-ended, that is, an apparatus, system, kit, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A prosthetic mold for forming a prosthesis having a bone mating surface, an articulating surface, and an intermedullary post, the mold comprising:

a first portion configured to form the articulating surface;
a second portion engageable with the first portion to define a mold cavity therebetween, the second portion configured to form the bone mating surface and define an intermedullary post cavity; and
an injection port configured to engage an injection assembly, the injection port extending outwardly from the second portion such that the injection port is axially aligned, and in communication, with the intermedullary post cavity.

2. The prosthetic mold of claim 1, further comprising a post-injection assembly configured to be removably coupled to the injection port, the post-injection assembly including a handle and a stem having at least one channel in fluid communication with the mold cavity, the at least one channel configured to permit a fluid to flow from the mold cavity into a hollow portion of the post-injection assembly.

3. The prosthetic mold of claim 1, further comprising at least one locking member configured to contemporaneously engage at least one first protrusion, disposed on the first portion, and at least one second protrusion, disposed on the second portion, to secure the first and second portions to each other.

4. The prosthetic mold of claim 3, the first and second portions further including a first and a second disengagement member, respectively, the at least one locking member configured to separately engage the first and the second disengagement member.

5. The prosthetic mold of claim 3, wherein the at least one locking member is configured to provide a planar surface for positioning the mold in an upright position.

6. The prosthetic mold of claim 1, wherein the second portion comprises:

a plunger configured to form the bone mating surface and define the intermedullary post cavity; and
a cover configured to fit over the plunger and engage the first portion.

7. The prosthetic mold of claim 6, wherein a position of the plunger, relative to the first portion, is adjustable among a plurality of positions between a predetermined maximum distance and a predetermined minimum distance.

8. The prosthetic mold of claim 7, further comprising an adjustment mechanism engaged with the plunger and configured to continuously adjust the plunger among the plurality of positions.

9. The prosthetic mold of claim 8, wherein the adjustment mechanism comprises a dial having a threaded surface configured to cooperate with a threaded surface of the plunger.

10. The prosthetic mold of claim 7, wherein the plunger further comprises a plurality of indicia corresponding to a plurality of dimensions of the mold cavity, as measured when the plunger is in one of the plurality of adjustable positions.

11. The prosthetic mold of claim 10, wherein the plurality of dimensions correspond to a plurality of distances between the bone mating surface and a region of the first portion corresponding to a low point in the articular surface of the prosthesis.

12. A prosthetic mold for forming a prosthesis having a bone mating surface and an articulating surface, the mold comprising:

a cavity member configured to form the articulating surface; and
a plunger having a surface configured to form the bone mating surface and a portion configured to form an intermedullary post having an injection port.

13. The prosthetic mold of claim 12, wherein the plunger comprises a plurality of vents in communication with the mold cavity.

14. The prosthetic mold of claim 12, further comprising an adjustment mechanism engaged with the plunger and configured to continuously adjust the plunger among a plurality of positions.

15. The prosthetic mold of claim 14, wherein the adjustment mechanism comprises a dial having a threaded surface configured to cooperate with a threaded surface of the plunger.

16. The prosthetic mold of claim 12, wherein the plunger further comprises a plurality of indicia corresponding to a plurality of dimensions of the mold cavity, as measured when the plunger is in one of a plurality of positions.

17. The prosthetic mold of claim 16, wherein the plurality of dimensions correspond to a plurality of distances between the bone mating surface and a region of the cavity member corresponding to a low point in the articular surface of the prosthesis.

18. The prosthetic mold of claim 12, further comprising a stop mechanism configured to engage the plunger to fix the position of the plunger within the mold cavity.

19. The prosthetic mold of claim 12, further comprising a compression mechanism engaged with the plunger, the cavity member, or both, and configured to press the plunger into the cavity member.

20. The prosthetic mold of claim 19, wherein the compression mechanism comprises a cover, an adjustment dial, or a compression rod.

* * * * *